(12) United States Patent
Schwerdhöfer et al.

(10) Patent No.: US 12,345,668 B2
(45) Date of Patent: Jul. 1, 2025

(54) MEASURING APPARATUS FOR THE ONLINE MEASUREMENT OF AT LEAST ONE PROPERTY OF PROCESS LIQUIDS AT AT LEAST TWO DIFFERENT FLOW RATES FOR THE PRODUCTION OF A MEDICAL LIQUID

(71) Applicant: VIVONIC GMBH, Sailauf (DE)

(72) Inventors: Jürgen Schwerdhöfer, Marktheidenfeld (DE); Stefan Eberlein, Höchberg (DE); Patrick Bessler, Erlenbach (DE)

(73) Assignee: VIVONIC GMBH, Sailauf (DE)

( * ) Notice: Subject to any disclaimer, the term of this patent is extended or adjusted under 35 U.S.C. 154(b) by 0 days.

(21) Appl. No.: 18/563,527

(22) PCT Filed: May 27, 2022

(86) PCT No.: PCT/EP2022/064406
§ 371 (c)(1),
(2) Date: Nov. 22, 2023

(87) PCT Pub. No.: WO2022/248664
PCT Pub. Date: Dec. 1, 2022

(65) Prior Publication Data
US 2024/0241069 A1 Jul. 18, 2024

(30) Foreign Application Priority Data
May 27, 2021 (DE) ..................... 10 2021 113 782.9

(51) Int. Cl.
*G01N 27/08* (2006.01)
*A61M 1/16* (2006.01)
*G01N 27/74* (2006.01)

(52) U.S. Cl.
CPC ........... *G01N 27/08* (2013.01); *A61M 1/1657* (2022.05); *A61M 1/1668* (2014.02); *G01N 27/74* (2013.01);
(Continued)

(58) Field of Classification Search
CPC ..... G01N 27/08; G01N 27/74; A61M 1/1668; A61M 1/1657; A61M 2205/3317; A61M 2205/3368
(Continued)

(56) References Cited

U.S. PATENT DOCUMENTS

| | | | |
|---|---|---|---|
| 5,015,389 A | 5/1991 | Portillo, Jr. | |
| 10,684,268 B2* | 6/2020 | Surman | G01N 33/2823 |

(Continued)

FOREIGN PATENT DOCUMENTS

| | | |
|---|---|---|
| CN | 110770176 | 2/2020 |
| DE | 69211124 | 1/1997 |

(Continued)

*Primary Examiner* — Raul J Rios Russo
*Assistant Examiner* — Trung Q Nguyen
(74) *Attorney, Agent, or Firm* — Kilyk & Bowersox, P.L.L.C.

(57) ABSTRACT

In order to reduce the number of redundant sensors for measuring a property of process liquids in liquid-carrying production systems, there is proposed a measuring apparatus (100) for the online measurement of at least one property of process liquids at at least two different flow rates and during the production of a medical liquid, which measuring apparatus has a tank (4) for receiving the process liquid, a hollow accumulation vessel (7), which is arranged within the tank (4), in a side wall of the tank (4) or on a side wall of the tank (4) and through which the process liquid can flow depending on the filling level in the tank (4), said accumulation vessel having at least one lower opening (20) and at least one upper opening (30) which are fluidically connected to the interior (Continued)

of the tank (4) such that process liquid can flow from the hollow accumulation vessel (7) into the tank, and a sensor (6) for measuring at least one property of the process liquid, which sensor is arranged in the hollow accumulation vessel (7).

18 Claims, 10 Drawing Sheets

(52) U.S. Cl.
CPC ............... *A61M 2205/3317* (2013.01); *A61M 2205/3368* (2013.01)

(58) Field of Classification Search
USPC ... 324/76.11, 600, 693, 500, 750.12, 750.21, 324/754.17, 754.29
See application file for complete search history.

(56) References Cited

U.S. PATENT DOCUMENTS

| | | | |
|---|---|---|---|
| 11,295,846 B2* | 4/2022 | Kamen | F04B 43/082 |
| 2013/0270165 A1* | 10/2013 | Shevitz | C12M 29/10 |
| | | | 210/205 |
| 2018/0055349 A1* | 3/2018 | Nguyen | B08B 3/08 |
| 2019/0154026 A1* | 5/2019 | Kamen | F04B 49/065 |
| 2020/0105546 A1* | 4/2020 | Kim | H01L 21/67023 |
| 2021/0268182 A1* | 9/2021 | O'Donnell | A61M 5/16804 |
| 2022/0184653 A1* | 6/2022 | Yang | B05C 11/1007 |
| 2023/0085052 A1* | 3/2023 | Klein | B01L 3/502738 |
| | | | 435/287.2 |

FOREIGN PATENT DOCUMENTS

| | | |
|---|---|---|
| DE | 102012018149 | 3/2014 |
| DE | 102014005430 | 10/2015 |
| EP | 2623188 | 8/2013 |

* cited by examiner

MEASURING APPARATUS FOR THE ONLINE MEASUREMENT OF AT LEAST ONE PROPERTY OF PROCESS LIQUIDS AT AT LEAST TWO DIFFERENT FLOW RATES FOR THE PRODUCTION OF A MEDICAL LIQUID

The present invention relates to a measuring apparatus for the online measurement of at least one property of process liquids at at least two different flow rates and during the production of a medical liquid,
- to a measurement system having such a measuring apparatus and at least two conduits for feeding at least two different process liquids and also to a controller,
- to a liquid-carrying production system for producing medical liquids, having such a measuring apparatus or such a
- and to a method for separately measuring at least one property of a process liquid using such a measuring apparatus, such a measurement system or such a liquid-carrying production system.

Liquid-carrying production installations are known in the fields of water technology, purified water preparation, reverse osmosis, dialysis water, dialysis concentrate and dialysis liquid, and also medical solutions. Examples of such production installations are purified water installations for providing dialysis water and dialysis concentrate mixing installations.

Particularly for the production of dialysis water, the relevant legal regulations and standards demand water quality monitoring and/or, for example, evidence for a specific retaining effect of contamination by a reverse osmosis membrane when operating a reverse osmosis installation or for a reverse osmosis membrane itself. Similar demands are placed on other purified water preparation installations. However, even in the case of most other fields and for most of the other installations there are specifications for a minimum in terms of sensor systems that the installations must include.

In addition to regulatory requirements, however, it is also decisive for the technical success of a liquid-carrying production system to ascertain measurement data in respect of the process liquids and control production processes on the basis of the measurement data.

Therefore, known liquid-carrying production systems usually have sensors for measuring properties of process liquids.

Known liquid-carrying production systems such as purified water installations that produce purified water for the dialysis by means of reverse osmosis comprise a plurality of identical sensors for measuring the same property of process liquids at different measurement sites. Thus, it may for example be the case that two, three, four or five sensors are arranged over the production system for the purposes of measuring the temperature and/or the conductivity of different process liquids or of process liquids in different production stages—e.g. before and after a filter stage. This serves to ascertain measurement data relating to the process liquid in different sections or stages. By way of example, in the region of the feedwater feed of reverse osmosis installations, the supplied liquids (not yet purified by reverse osmosis), especially water with different quality levels, are known to be fed to sensors for measuring conductivity and temperature of the water.

A problem of known liquid-carrying production systems is that they require a plurality of identical sensors for measuring the same property of a plurality of different process liquids or of the same process liquid at different flow rates, sometimes even for both cases. Arranging a plurality of identical sensors for measuring the same property of process liquids leads to various disadvantages or problems. It leads directly to a higher product price of a liquid-carrying production system. Redundant sensors generate high additional costs. Moreover, the production system becomes structurally more complicated and larger in terms of size since each sensor requires space for the arrangement, a link to a power supply and a controller, as well as constructive measures. A further problem consists in the need of comparing the various sensors to one another in order to obtain consistent measurement data. In practice, a complete comparison is not possible on account of the constructive peculiarities and/or large spacings of the sensors from one another. Very different flow rates are expected for different process liquids of known liquid-carrying production systems. Known measuring apparatuses for liquids are only set up for measuring a property of a liquid over a relatively narrow range, and so they are only suitable for measuring one process liquid.

It is an object of the present invention to reduce the severity of or completely avoid the problems known from the prior art. Thus, for example, it is an object of the present invention to reduce the number of redundant sensors for measuring a property of process liquids in liquid-carrying production systems.

This object is achieved by a measuring apparatus for the online measurement of at least one property of process liquids at at least two different flow rates comprising a tank and a hollow accumulation vessel according to claim 1 and by a method for separately measuring at least one property of a process liquid according to claim 13. Configurations and developments of the inventive concept are the subject matter of dependent claims.

The measuring apparatus for the online measurement of at least one property of a process liquid at at least two different flow rates and during the production of a medical liquid comprises
- a tank for receiving the process liquid, wherein the tank has an outflow,
- a hollow accumulation vessel which
  - i.) is arranged within the tank, in a side wall of the tank or on a side wall of the tank,
  - ii.) depending on the fill level in the tank can have process liquid pass therethrough, can be entirely filled by process liquid or can be partly filled by process liquid,
  - iii.) has at least one lower opening, which is arranged in the lower region of the hollow accumulation vessel and fluidically connected to the interior of the tank, process liquid stored in the hollow accumulation vessel being able to flow into the tank through said opening in the case where a fill level of the tank is lower than the fill level in the hollow accumulation vessel,
  - iv.) has at least one upper opening, which is arranged in the upper region of the accumulation vessel and fluidically connected to the interior of the tank such that additionally process liquid can overflow out of the hollow accumulation vessel through the upper opening into the tank, the fill level of the process liquid in the hollow accumulation vessel reaches up to at least one upper opening,
  - v.) wherein the upper region is located above the lower region, vi.) wherein the sum of the cross sections of the upper openings is at least ten times as large as the sum of the cross sections of the lower openings, a sensor for measuring at least one property of the process liquid, which sensor is arranged in the hollow accumulation vessel in such a way that it can be in contact with the process liquid when process liquid accumulates in the hollow accumulation vessel.

As a result of the geometric design of the hollow accumulation vessel and its lower and upper openings, the measuring apparatus according to the invention is particularly advantageously embodied to nevertheless be able to wet the sensor with liquids flowing in at different flow rates and to thus allow one of the properties of said liquids to be measured by the sensor. This makes it possible to measure process liquids flowing at different flow rates using the same sensor. Since different process liquids frequently occur with different flow rates, this also allows different process liquids to be measured at different flow rates in respect of one property. The design of the hollow accumulation vessel allows measurements to be carried out over a range of flow rates, with the maximum flow rate being at least ten times as high as the minimum flow rate.

In addition to overcoming the problems in the prior art, a further advantage of the solution according to the invention lies in the fact that a possibly complicated comparison of different sensors at different sites in an apparatus is dispensed with because the same sensor measures different liquids.

A further advantage of this design of the measuring apparatus according to the invention lies in the fact that existing systems can be retrofitted therewith. In this case, hydraulic actuators, etc., can be maintained and the software of a controller would have to be updated.

A further advantage of the measuring apparatus according to the invention lies in the fact that parameters of various process steps of a liquid-carrying production system can be captured using only one and the same sensor by virtue of the process liquids corresponding to the respective process steps being fed to the one sensor in the measuring apparatus.

A further advantage of the measuring apparatus according to the invention lies in the fact that it can be integrated in existing liquid-carrying production systems or measurement systems at a later stage by way of retrofitting. Since, as a rule, such installations already have conduits, controllers and actuators, the measuring apparatus according to the invention can be retrofitted by replacing a tank. The hollow accumulation vessel with its openings and the sensor are arranged in the tank. The hollow accumulation vessel need only be designed or positioned so as to fit to the existing installation so that the process liquids to be measured can reach into the hollow accumulation vessel. The measuring apparatus according to the invention offers a multiplicity of geometric arrangement options and is adaptable to very many existing systems as a result. Finally, it is only necessary to adapt the control software in the controller in order to use existing actuators to feed liquid flows to the hollow accumulation vessel for measurement purposes and it is necessary to connect the sensor in the accumulation vessel to the controller.

An essential aspect of the invention lies in the provision of a hollow accumulation vessel for a sensor, said accumulation vessel being equipped with openings so that it is possible to measure both liquids with low flow rates and liquids with high flow rates. Consequently, one sensor suffices to cover different liquids and/or very different flow rates of process liquids. To this end, the openings and the hollow accumulation vessel are configured such that they act both as a means for accumulation and as a means facilitating the overflow. An accumulation effect is necessary because certain sensors or certain measuring procedures require a sensor to be submerged in the liquid to be measured. By way of example, this applies to certain conductivity sensors. Accordingly, the hollow accumulation vessel presented here particularly advantageously facilitates the damming of process liquids with low flow rates.

What is essential to the measuring apparatus presented here is that the hollow accumulation vessel is designed such that inflowing liquids can be reliably fed to the sensor arranged in the hollow accumulation vessel over a large range of flow rates—the maximum being at least one order of magnitude greater than the minimum. In the case of low flow rates, the vessel dams the liquids flowing therethrough by means of the only relatively small cross section of the lower opening. In the case of high flow rates, the fill level in the hollow accumulation vessel rises until additionally dammed liquid can be discharged through an upper opening. If the fill level of the tank in which the accumulation vessel is situated increases, water can flow from the tank into the accumulation vessel through the openings and hence reach the sensor. This applies analogously if the hollow accumulation vessel is situated on a wall or in a wall of the tank. As a result of this geometric nature and arrangement, the measuring apparatus facilitates the measurement of different liquids with different flow rates.

The method for separately measuring at least one property of at least two different process liquids at different flow rates by the same sensor using a measuring apparatus, a measurement system or a liquid-carrying production system according to the invention includes at least the following steps:

a. separately feeding the process liquid to be measured to the sensor in the hollow accumulation vessel,
b. measuring a property of the process liquid in contact with the sensor until a predetermined minimum measurement time has been reached,
c. storing the measurement value of the property of the process liquid after the predetermined minimum measurement time has been reached.

This particularly advantageously ensures that only one process liquid in each case is supplied separately to the sensor of the measuring apparatus at a given measurement time.

Furthermore, this advantageously ensures that no unknown mixture of process liquids is measured.

In a particularly advantageous embodiment of a measuring apparatus as proposed here, the sensor is a conductivity sensor or temperature sensor. This particularly advantageously facilitates economizing of redundant sensors of these types. Both the temperature and the conductivity of liquids are important parameters in the field of liquid-carrying production systems. These parameters can be decisive variables for the production operation. The provision of at least one of these sensor types for measurement purposes is often required, particularly in the field of medical liquids. By way of example, this also applies to purified water installations, for example for dialysis, but also to dialysate and dialysate concentrate production installations. In the case of the conductivity sensor, this additionally yields the advantage of considerable savings of costs if redundant sensors can be economized. This is because conductivity sensors often require increased outlay: Feeding a measuring cell of a sensor with a variable alternating current source and subsequently preparing the measurement values is technically complicated and the physical components required to this end are expensive. This applies, in particular, if each liquid to be assessed requires very spaced apart installation positions and a complete measurement path, consisting of cell, wiring and measuring transducer, is required.

In a particularly advantageous embodiment of a measuring apparatus as proposed here, two or more sensors are arranged together in the hollow accumulation vessel for the purposes of measuring different properties of the process liquid. This particularly advantageously allows economizing of redundant sensors for different properties of the process liquids to be measured. Moreover, this particularly advantageously allows relevant properties of the liquids to be measured together at the same location.

In a particularly advantageous embodiment of a measuring apparatus as proposed here, both a conductivity sensor and a temperature sensor are arranged together in the hollow accumulation vessel. This combination is particularly advantageous in the field of medical liquids since both properties of liquids need to be measured in many cases.

In a particularly advantageous embodiment of a measuring apparatus as proposed here, the hollow accumulation vessel has a shape that tapers from top to bottom, a funnel shape or a cylindrical shape. A shape the tapers from top to bottom and a funnel shape are particularly well suited to wetting a sensor in the lower region, even in the case of low flows, while the greater cross section up top advantageously comes to bear in the case of greater flows. A cylindrical shape is particularly advantageously cost-effective in production and easy to handle.

In a particularly advantageous embodiment of the invention, it is proposed to integrate the measuring apparatus according to the invention in a measurement system. In addition to the measuring apparatus, the measurement system has at least two conduits for feeding at least two different process liquids into the tank, at least two means for controlling the feed or discharge of process liquids into the tank and a controller. The controller is configured to capture the measurement values of the sensor and control the valves. Means for controlling the feed or discharge relate to active hydraulic actuators such as valves, switches or pumps. An occluding pump blocks one conduit when at a standstill and releases one conduit during operation. These actuators release a conduit or block a conduit and, as a result, control the flow in the respective conduit. If a certain liquid needs to be measured, what active actuators can particularly advantageously facilitate is the supply of this process liquid to the tank of the apparatus—and hence also to the sensor—for measurement purposes within a short reaction time. Moreover, the combination of the measuring apparatus with the further elements of the measurement system can particularly advantageously be used autonomously. If there is an existing liquid-carrying production system but pure retrofitting of a measuring apparatus according to the invention is neither intended nor possible, it is advantageously possible instead to retrofit a measurement system according to the invention. This advantageously dispenses with having to equip a controller with updated software at a later stage. Moreover, this advantageously ensures that conduits, means for controlling the flow of the process liquids and a controller go well together with the measuring apparatus according to the invention or the operation thereof.

In a particularly advantageous embodiment of a measurement system as proposed here, the at least two conduits are arranged so that a freefall path is formed in each case between their outlet openings at the end and the hollow accumulation vessel. This is accompanied by the particular advantage of the measurement system being set up in particularly hygienic fashion. There cannot be unwanted mixing or contamination between the conduits and nor can a backflow from the tank into one of the conduits result in unwanted mixing or contamination.

A particularly advantageous embodiment of a measurement system as proposed here comprises one or more of the following means for identifying which process liquid is in contact with the sensor of the measuring apparatus:
   a. at least one means for determining the fill level in the tank, which means is able to identify more than two differently high fill levels in the tank,
   b. or at least two fill level limit switches which are set up to determine a lower and an upper fill level in the tank,
   c. or the controller is set up to control the flow of the different process liquids in a certain time sequence so that the current process liquid can be determined on the basis of the time profile,
   d. or, if the measurement region of the properties of the process liquid is non-overlapping for the different process liquids, the controller is set up to carry out an assignment of measurement value to process liquids on the basis of the measurement value of the sensor and known measurement regions for different process liquids.

This particularly advantageously allows measurement values to be assigned to different process liquids. In turn, this advantageously allows, firstly, a plausibility check to be carried out on the basis of the expected measurement values and, secondly, storing of measurement values with an assignment to the respective liquid.

In a particularly advantageous embodiment of the invention, it is proposed to integrate the measuring apparatus according to the invention or the measurement system according to the invention in a liquid-carrying production system for producing medical liquids. Particularly advantageously, the invention can act as an integrated component of a liquid-carrying production system and can reduce costs and improve the measurement quality there by virtue of dispensing with redundant sensors and by virtue of rendering a comparison obsolete because the same sensor measures at least one property of different process liquids.

A particularly advantageous embodiment of a liquid-carrying production system as proposed here is embodied as a water treatment installation or a purified water preparation installation for providing dialysis water. In this example, the measuring apparatus is arranged in a reservoir tank of the production system. Since most if not all process liquids of such a system flow in or through a reservoir tank, this particularly advantageously allows the number of redundant sensors to be reduced, possibly even for a plurality of properties of process liquids at the same time. Further advantageously, this dispenses with the need of comparing the economized redundant sensors with respect to one another, which may otherwise be connected with particular complexity. A yet again particularly advantageous embodiment of such a liquid-carrying production system is embodied as a reverse osmosis installation. The aforementioned advantages apply to a particular extent here since these sensors are required by standards. However, a realization that avoids unnecessary redundancies is admissible and can contribute significantly to the commercial success of such a system.

A particularly advantageous embodiment of a liquid-carrying production system as proposed here is embodied as a mixing installation for providing dialysis fluid or dialysis fluid concentrate. Here, the measuring apparatus is arranged in a reservoir tank or mixing tank of the production system.

Since most if not all process liquids of such a system flow in or through a reservoir tank, this particularly advantageously allows the number of redundant sensors to be reduced, possibly even for a plurality of properties of process liquids at the same time. Further advantageously, this dispenses with the need of comparing the economized redundant sensors with respect to one another, which may otherwise be connected with particular complexity.

In a particularly advantageous embodiment of a method as proposed here, the separate feed is implemented with at least the following steps:
  a. lowering the fill level in the tank until the fill level is below the hollow accumulation vessel,
  b. releasing the conduit for feeding the process liquid to be measured into the hollow accumulation vessel.

This particularly advantageously ensures that liquid still situated in the tank is not inadvertently measured by the sensor in the hollow accumulation vessel. Further advantageously, exactly the liquid fed by the released conduit is measured.

In a particularly advantageous embodiment of a method as proposed here, the separate feed is implemented with at least the following steps:
  a. raising the fill level in the tank up to a fill level that is level with the sensor or higher.

As a result, the process liquid present in the tank, which in turn may be a mixture of process liquids, can particularly advantageously be measured. Furthermore, if there is a dynamic shift in the mixing ratios of the liquid in the tank, this shift can particularly advantageously be dynamically understood as a result, thanks to the online measurement.

In a particularly advantageous embodiment of a method as proposed here, at least one property of at least two different process liquids is measured with the same sensor, wherein successively in an interchangeable sequence at least one property of a first process liquid is measured using a method according to the invention with lowering the fill level in the tank of the apparatus according to the invention and feeding by releasing the conduit for feeding a process liquid and at least the same property of a second process liquid is measured using a method with raising the fill level in the tank and thereby establishing a feed to the sensor or wherein a second process liquid is fed again for the measurement with the same sensor by way of a feed by means of releasing a conduit for feeding a process liquid, but this time with a different conduit than the conduit of the first measured process liquid. This particularly advantageously allows different process liquids to be measured in succession in respect of at least one property using the same sensor. By way of the successive measurements, there can once again advantageously be a comparison of the measured property of the liquids. Advantageously, two or more process liquids can be fed to the sensor from conduits and/or one process liquid can be fed to the sensor via the tank fill level and another process liquid can be fed to the sensor via a conduit. Hence, many process liquids and process steps for producing a liquid-carrying production system are able to be covered.

In a particularly advantageous embodiment of a method as proposed here, the separate feed is implemented following the lowering of the fill level in the tank by virtue of the process liquid remaining in the tank being guided to a reverse osmosis membrane and either the liquid that passed through the reverse osmosis membrane or the process liquid that did not pass through the reverse osmosis membrane being fed to the sensor. In the case of a reverse osmosis installation, this particularly advantageously allows measurement of a property of produced purified water, which passed through the membrane, or of the water remaining in front of the membrane during purification.

In a particularly advantageous embodiment of a method as proposed here, at least one property of at least two different process liquids is measured using the same sensor, as described further above, and there additionally is a further measurement and a comparison with a second sensor. Here, the method additionally comprises at least the following steps:
  a. separately feeding the process liquid to be measured to the second sensor,
  b. measuring the same property of the process liquid in contact with the second sensor until a predetermined minimum measurement time has been reached,
  c. storing the measurement value of the property of the process liquid after the predetermined minimum measurement time has been reached,
  d. comparing the measurement values of the two sensors.

This particularly advantageously allows a sensor used in multifaceted ways to additionally be checked by comparison with a further sensor. Further advantageously, in the case of a liquid-carrying production system for medical liquids, a confirmation of the measurement values from the tank with additionally a further sensor situated downstream is facilitated. This can ensure that the medical liquid produced also has the required quality downstream thereof.

In a particularly advantageous embodiment of the invention, a measurement system or a liquid-carrying production system has a controller that is configured to carry out a method according to the invention. This particularly advantageously ensures that the apparatus according to the invention is separately fed with process liquids to be measured, in accordance with the method.

The hollow accumulation vessel can also be arranged in the lid of the tank of the measuring apparatus according to the invention instead of in or on a side wall.

In all embodiments of the invention, a sensor for measuring at least one property of the process liquid is arranged in the hollow accumulation vessel in such a way that it is in contact with the process liquid when process liquid accumulates in the hollow accumulation vessel. Preferably, the sensor is arranged below the upper opening or the upper openings. So that the sensor comes into contact with the process liquid to be measured or said sensor can even be entirely wetted by the process liquid even in the case of low flow rates, the sensor is even further preferably arranged in the lower region of the hollow accumulation vessel or adjacent to the lower region of the hollow accumulation vessel.

As a result of the sum of the cross sections of the upper openings of the hollow accumulation vessel being at least ten times as large as the sum of the cross sections of the lower openings, process liquid can flow through all of the upper openings with ten times the flow rate in comparison with the flow through all of the lower openings. This assumes that the openings of the hollow accumulation vessel all have a macroscopic extent, i.e. not precisely so small that capillary effects or surface tension has a significant influence on the flow rate or a flow resistance. Thus, this does not mean nanometre scale openings. Moreover, the assumption is made here that the viscosity of the process liquids ranges from one order of magnitude smaller to one order of magnitude greater than the viscosity of liquid water. This means viscosities ranging from approximately 0.25 mPa s to approximately 25 mPa s, i.e. not a highly viscous liquid such as pure glycerol. The possible flow rate through openings of such liquids is decisively determined by the size of the openings. In addition to water with different temperatures and degrees of purity, aqueous solutions of salts and/or other electrolytes, as occur during the production of medical liquids such as isotonic salines, medical rinsing solutions and, in particular, dialysis fluid and dialysis concentrate as a process liquid, preferably also come into question as process liquids. Dialysis concentrate denotes a medical liquid from which it is possible to produce dialysis fluid at the treatment location by mixing with purified water or dialysis water.

The at least one lower opening of the measuring apparatus, which is arranged in the lower region of the hollow accumulation vessel and which is fluidically connected to the interior of the tank, can be considered to be the drain of the hollow accumulation vessel. This is because a process liquid can flow from the interior of the hollow accumulation vessel of the measuring apparatus into the interior of the tank through the at least one lower opening if the fill level of the tank is lower than the fill level in the hollow accumulation vessel. In this case, process liquid accumulated in the hollow accumulation vessel can drain into the tank. There can also be a plurality of lower openings. The same applies if the hollow accumulation vessel comprises a plurality of lower openings. In this case, it is not necessary for all lower openings to be at the same level. All lower openings are located in the lower region of the hollow accumulation vessel.

The at least one upper opening of the measuring apparatus, which is arranged in the upper region of the hollow accumulation vessel and which is fluidically connected to the interior of the tank, can be considered to be an overflow opening. This is because a process liquid can flow from the interior of the accumulation vessel into the interior of the tank through the at least one upper opening if the level/fill level in the hollow accumulation vessel reaches up to one or more upper openings. Then, process liquid can additionally overflow from the hollow accumulation vessel into the tank through the upper opening. This is because the upper opening is fluidically connected to the interior of the tank. The level/fill level in the hollow accumulation vessel can increase if more process liquid flows into the hollow accumulation vessel than drains through the at least one lower opening. Then, the incoming flow of the liquid brings about an increase in the level/fill level in the hollow accumulation vessel. However, the level/fill level may still be high enough for process liquid to flow out through the upper openings even if it is not the case that more process liquid flows in than can drain through the lower openings. There can also be a plurality of upper openings. The same applies if the hollow accumulation vessel comprises a plurality of upper openings. In this case, it is not necessary for all upper openings to be at the same level. All upper openings are located in the upper region of the hollow accumulation vessel.

In this case, an online measurement means that a liquid is measured as it flows by, i.e. without a sample being taken.

In the context of this technical disclosure, top and bottom are unambiguous since this relates to the handling of liquids in the presence of gravity. Consequently, it is clear that in the case of an empty tank or accumulation vessel liquid initially collects at the bottom during the filling procedure and then continues to rise when being dammed or filled so that the surface of the liquid rises, i.e. reaches further in the upward direction. Preferably, top and bottom refer to the orientation of the measuring apparatus in the installation position. For example, the outflow of the tank is located at the bottom in the installation position.

The upper opening and the lower opening can have any form. In this case, it is irrelevant whether the openings are equipped with an individually assignable edge that defines the opening, for example in the case of a circular drilled hole—around which a circular edge is then formed —, or whether the openings are partly defined without an edge, for instance in the case of a slot which directly merges into a larger opening, for example at one end. To work, it is necessary for the openings to be large enough for the liquid to be able to pass therethrough, i.e. for these openings not to be so small that the liquid cannot pass therethrough on account of its capillary forces or molecular size. To work, what is moreover essential is that the openings enable a passage from the hollow accumulation vessel into the tank, i.e. that these openings are not just depressions in the wall but through-holes.

In the context of the present disclosure, sensors and measuring apparatuses for measuring the electrical conductivity of a liquid can comprise a measuring cell containing electrodes and driver and evaluation electronics. Here, all aforementioned components or only driver and evaluation electronics can be combined in a so-called measuring transducer. Optionally, the conductivity measuring cell can additionally comprise a temperature sensor such as a resistance thermometer or a semiconductor temperature sensor, for example. In the direct vicinity of the electrodes, the evaluation electronics process the raw measurement signal into a processed measurement signal, which can be transmitted to a controller or a further evaluation unit.

Preferably, the measuring apparatus presented here or the measurement system is set up so that a third separate process liquid can be measured, the latter not being fed directly to the sensor from a conduit but reaching the sensor via the fill level in the tank. In the case of a sufficiently high fill level in the tank, the process liquid situated in the tank penetrates up to the sensor through the holes in the hollow accumulation vessel. The process liquid in the tank can be, for example, a mixture of other process liquids which can be fed via conduits, for example. In this variant, it is necessary for the tank to be able to accumulate. All embodiments require the interior of the tank to be in fluidic connection with the interior of the hollow accumulation vessel.

Preferably, the geometry of tank and hollow accumulation vessel allows various process liquids in the tank to be mixed. By way of example, mixing may be desirable if no property of a process liquid is currently being measured or if a property of a mixture of process liquids is measured.

Dialysis water is purified water suitable for preparing dialysis fluid—also referred to as dialysate. Dialysis is a kidney replacement treatment. This refers to both haemodialysis and peritoneal dialysis. Dialysis water is frequently produced by virtue of tap water running through various filter stages. Contaminations and water hardness are removed in the process. Here, reverse osmosis is often used in one filter stage. Therefore, one process liquid can preferably be so-called soft water, for example, which has already passed through various filter stages, for example a coarse filter and an active charcoal filter, and whose water hardness has been reduced in a water softener. This soft water is then frequently pressed through a reverse osmosis membrane in order to provide purified water. In this case, the purified water can also be referred to as reverse osmosis water. Reverse osmosis is abbreviated RO. Therefore, reverse osmosis water is often referred to as RO water. Reverse osmosis water or RO water can also be a process liquid within the context of the invention.

In the context of the present disclosure, examples of liquid-carrying production systems are compact reverse osmosis installations which are adapted to the production of purified water for dialysis (also referred to as dialysis water), for example. Such installations can be dimensioned so compactly that they are portable, equipped with rollers and, for example, the size of a suitcase. Such installations can be designed to be able to supply a single treatment device for haemodialysis or peritoneal dialysis. However, they may also be slightly more powerful and be designed for the supply of up to four or five such treatment machines. By way of example, such production systems can comprise sensors for measuring the properties of the following process liquids:

intake water (which is fed to the production system and possibly has already passed through a coarse filter stage) or soft water (if it has passed through a stage for reducing the water hardness), the purified water feed, the return of unused purified water from a ring conduit with consumers (also purified water return—wherein purified water in the context of reverse osmosis is also referred to as permeate since it was pressed through the reverse osmosis membrane), and the so-called feedwater or mixed water, which may be, for example, a mixture of input water and purified water return and which is called thus because it is used to feed the reverse osmosis membrane. Feedwater or mixed water can also be referred to, for example, as a mixture of two or more process liquids such as soft water, water retained during purification at the membrane (also referred to as retentate) and purified water, which may be situated in a tank of a measuring apparatus as presented here. A return for purified water is common and even obligatory in certain configurations. In this case, purified water that was produced and not taken by the connected consumers is returned—for example via a ring conduit or a return conduit. For such production systems, flow rates of intake water or soft water of 200-1500 litres/hour, of purified water return of 10-300 litres/hour and of feedwater or mixed water of 600-1200 litres/hour come. In this example, the flow rate to be expected is to the range of 10-1500 litres per hour. The maximum value of the flow rate is 150 times greater than the minimum value. Nevertheless, the technical solution disclosed here renders it possible to measure a property of a plurality of process liquids over the entire range of flow rates. This is facilitated by virtue of an embodiment of the hollow accumulation vessel being designed in such a way that the sum of the cross sections of the upper openings is 150 times larger than the sum of the cross sections of the lower openings.

Examples of liquid-carrying production systems in the context of the present disclosure are central reverse osmosis installations, which are adapted, for example, to the production of purified water for dialysis (also referred to as dialysis water) for supplying a multiplicity of dialysis machines in a hospital or in a dialysis centre. By way of example, this allows ten or 30 or 50 haemodialysis treatment machines to be supplied simultaneously. By way of example, such liquid-carrying production systems are installed in stationary fashion in a supply room and extend over several square metres.

By way of example, such production systems can have sensors for measuring the properties of the following process liquids: intake water or soft water, if it has passed through a stage for reducing the water hardness, the purified water feed, the return of unused purified water from a ring conduit with consumers (also referred to as purified water return) and feedwater or mixed water. By way of example, mixed water refers to a mixture of two or more process liquids such as soft water, water retained during purification at the membrane (also referred to as retentate) and purified water, which may be situated in a tank of a measuring apparatus as presented here. By way of example, if unconsumed, purified water can be returned following the pass through a distributor conduit with consumers. For such production systems, flow rates of intake water or soft water of 2000-8000 litres/hour, of purified water return of 100-400 litres/hour and of feedwater or mixed water of 2500-20,000 litres/hour occur. In this example, the flow rate to be expected is to the range of 100-20,000 litres per hour. The maximum value of the flow rate is 200 times greater than the minimum value.

In an exemplary case assumed to occur quite frequently in practice, a liquid-carrying production system typically produces 4000 litres of purified water per hour. With a water-related effectiveness of 50%, 8000 litres of soft water are required each hour for this production. The maximum flow rate of a mixed water process liquid could be 12,000 litres per hour, the maximum flow rate in this example. By contrast, the return of unconsumed purified water will only be 400 to 800 litres per hour. Hence, the maximum flow rate is 30 times higher than the minimum flow rate.

In a further example from practice, the flow rate for soft water as a result of a reduction in capability due to the pre-filtration might be no more than 6000 litres per hour and, at the same time, the return of unconsumed purified water is never less than 600 litres per hour. Then, the maximum flow rate would be 10 times higher than the minimum flow rate.

All embodiments of the invention can be designed such that two different process liquids are fed to the hollow accumulation vessel via conduits ending thereabove and the third process liquid is fed via raising the fill level of the liquid in the tank.

Nevertheless, the technical solution disclosed here renders it possible to measure a property of a plurality of process liquids over the entire range of flow rates. This is facilitated by virtue of an embodiment of the hollow accumulation vessel being designed in such a way that the sum of the cross sections of the upper openings is 200 times larger than the sum of the cross sections of the lower openings.

In one variant of the measuring apparatus or of the measurement system, the supply of the process liquids to be measured is set up such that a plurality of conduits opens into one another upstream of the end opening of the conduit. As a result, a plurality of process liquids can advantageously reach the hollow accumulation vessel through the same conduit end section.

In a preferred embodiment, a purified water installation for the production of dialysis water by means of reverse osmosis has a measuring apparatus. The measuring apparatus is set up to measure the temperature and conductivity properties of two, three or four different process liquids of this liquid-carrying production system. By way of example, the liquids fed are the feedwater that is fed to the production system, produced but unconsumed purified water (referred to as permeate in the case of a reverse osmosis installation), which is returned for example to the purified water installation, and a mixture of liquids in the tank in which the measuring apparatus is arranged.

A controlled separate feed of a process liquid to be measured is essential to the invention. It should also be noted that the so-called feedwater or mixed water is also considered a separate process liquid in the context of the invention, even though this is a mixture of a plurality of process liquids: At the time of the measurement using the sensor, only this process liquid is in contact with the sensor in a controlled manner.

The measurement system or liquid-carrying production system according to the invention can have means for storing data, for example a memory card or hard disk drive.

Further advantages, features and effects of the present invention arise from the following description of preferred embodiments of the invention, where reference is made to the figures in which the same or similar components are denoted by the same reference sign.

BRIEF DESCRIPTION OF THE DRAWING

The apparatuses and methods are described below with reference to the drawing. In the drawing:

FIG. 4 shows three further different embodiments of the measuring apparatus according to the invention with differently designed shapes of the tank and hollow accumulation vessel, wherein each of the three embodiments is shown in turn in three different partial views in each case.

In the figures, the same or similar elements can be referenced by the same reference sign.

FIG. 1 shows an exemplary embodiment of a measuring apparatus 100 according to the invention in the context of a measurement system 300. An exemplary hollow accumulation vessel 7 has a shape corresponding to a lateral cylinder wall in the lower region 25 and a skewed funnel in the upper region 35. The exemplary hollow accumulation vessel 7 is arranged in a tank 4, for example has a lower opening 20 in the lower region 25 and for example three to eight upper openings 30 in the upper region 35. A sensor 6 for measuring at least one property of a process liquid is arranged such that it can be in contact, i.e. in the measurement contact, with a liquid accumulating in the hollow accumulation vessel 7. In the exemplary embodiment of the measuring apparatus 100 shown, the hollow accumulation vessel 7 is arranged on a side wall in the interior of the tank 4. Since the highest point of the hollow accumulation vessel 7 is lower than the upper edge of the tank 4 in this embodiment, process liquid can also flow into the tank 4 over the edge of the funnel-shaped upper portion 35 of the hollow accumulation vessel 7.

In FIG. 1, electrical connections are shown as dotted lines and hydraulic conduits are shown as full lines. This also applies to FIGS. 2 and 6.

Figure 1:
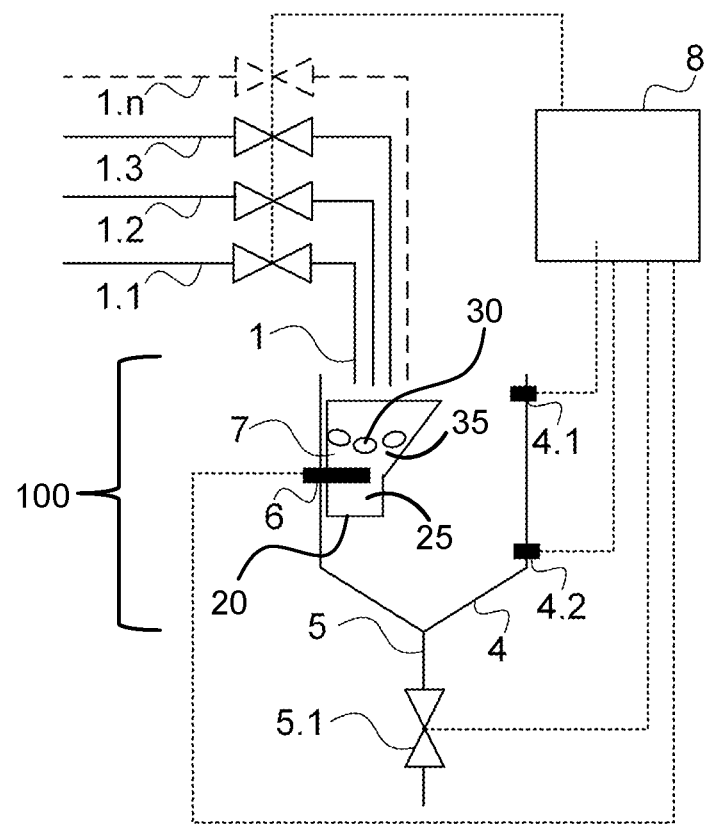
FIG. 1 shows the measuring apparatus according to the invention for the online measurement of at least one property of process liquids at at least two different flow rates, having a hollow accumulation vessel in a tank in a first embodiment in a measurement system according to the invention of an exemplary embodiment.

The measuring apparatus 100 is shown in FIG. 1 as part of an exemplary measurement system 300. The measurement system has a controller 8 which, in exemplary fashion, is not only connected in this case to the sensor 6 but also to an upper fill level limit switch 4.1 and a lower fill level limit switch 4.2 and to a plurality of check valves, e.g. the valve 5.1 in the conduit 5 at the outlet connector of the tank 4. Three conduits 1, 1.1, 1.2, 1.3 for three process liquids are arranged in such a way that their end openings are situated above the hollow accumulation vessel 7. In this case, the conduits reach into the tank 4 and have a small distance from the hollow accumulation vessel 7 such that a freefall path is formed.

Figure 2A:
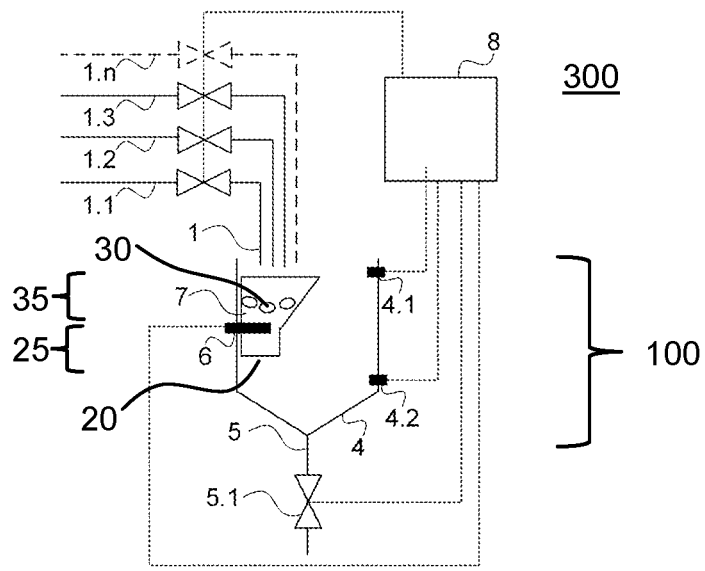
FIG. 2 shows the same measuring apparatus according to the invention with a tank as part of the same measurement system according to the invention as in FIG. 1, wherein different fill levels of the tank are shown in three different partial views FIG. 2a, FIG. 2b, FIG. 2c.
Figure 2B:
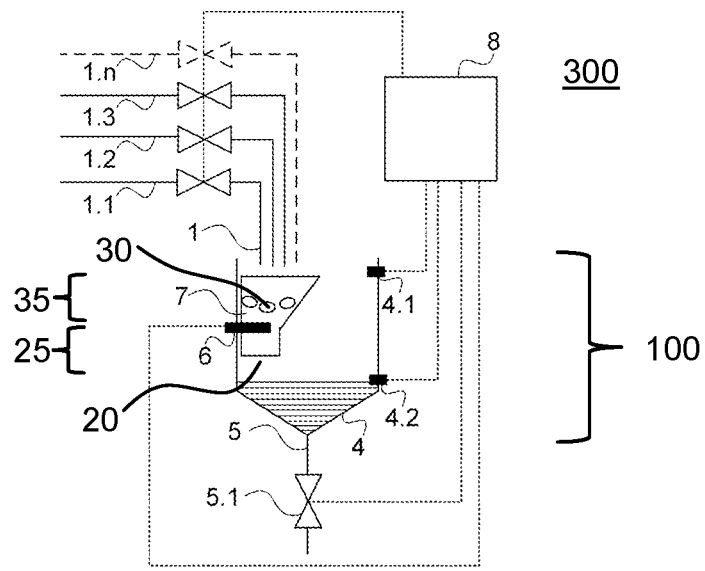
Figure 2C:
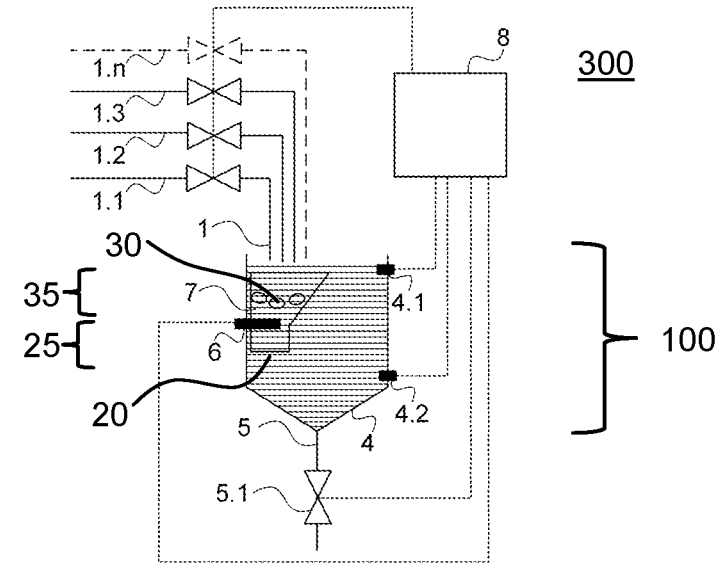
Figures 1, 3A:
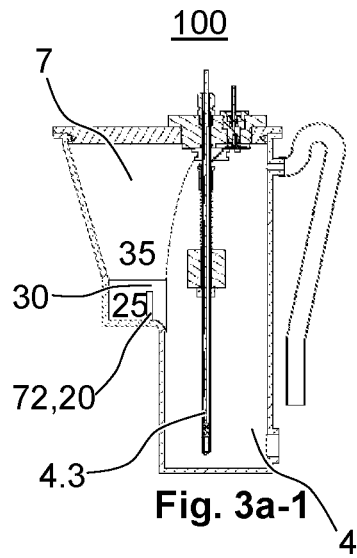
Figures 1, 3B:
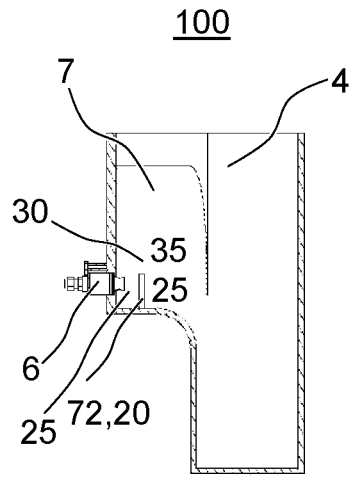
Figures 1, 3C:
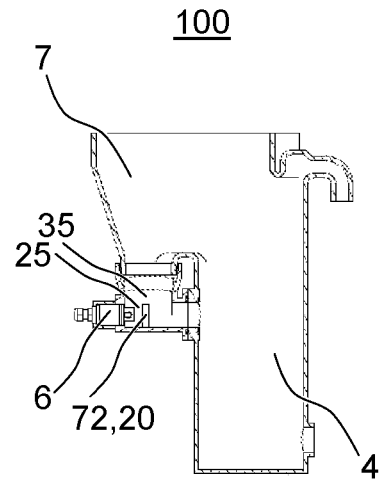
Figures 2, 3A:
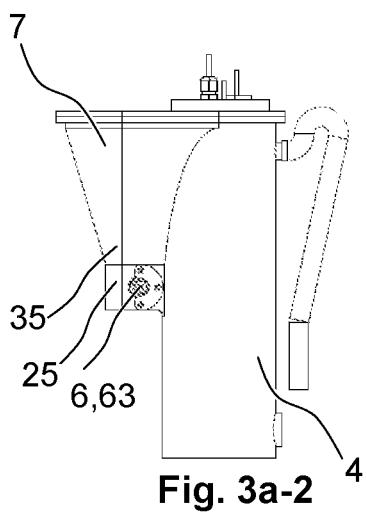
Figures 2, 3B:
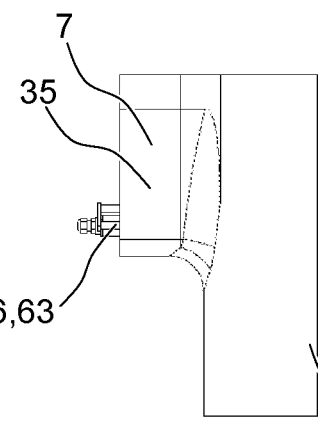
Figures 2, 3C:
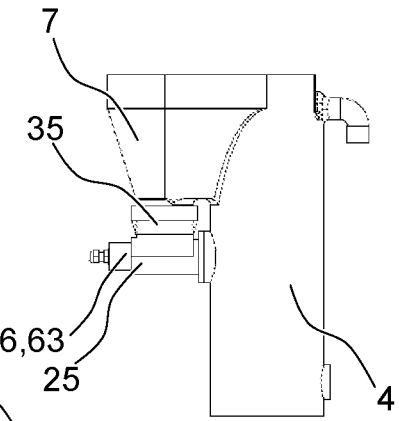

FIG. 2 shows the exemplary embodiment of a measuring apparatus 100 according to the invention in the context of a measurement system 300 of FIG. 1 with three different fill levels of the tank 4 on one page of the drawing for a better illustration. Thus, FIG. 2a shows an empty tank 4 and hence it shows the same as in FIG. 1, albeit in a smaller illustration. FIG. 2b shows a fill level that only reaches to the exemplary lower fill level limit switch 4.2. In this case, the hollow accumulation vessel 7 of the measuring apparatus 100 is not submerged in the liquid in the tank 4. The fill level in the tank 4 lies below the hollow accumulation vessel 7. However, other means for capturing the fill level could optionally also be provided in interchangeable fashion, for example a means for measuring a multiplicity of discrete fill levels using reed sensors or a continuous fill level measurement. FIG. 2c shows a high fill level that almost reaches to the upper edge of the tank 4 and the upper fill level limit switch 4.1. In this case, the hollow accumulation vessel 7 of the measuring apparatus 100 is below the fill level in the tank, i.e. completely submerged in the process liquid.

FIGS. 3a, 3b, 3c, 4a, 4b and 4c show exemplary embodiments of the measurement system disclosed here in different geometric designs. All six exemplary embodiments shown have at least one lower opening 20 in the lower region 25 of the hollow accumulation vessel 7. By way of example, the lower opening 20 can be embodied as a circular drill hole or as a slot. Optionally, the lower opening 20 is formed in a wall section 72 in the lower region 25 of the hollow accumulation vessel 7. Preferably, the lower opening 20 is embodied as a slot which extends to the base or the lowermost point of the interior of the hollow accumulation vessel 7. This particularly advantageously allows, firstly, process liquid to be able to emerge from the hollow accumulation vessel 7 through the lower opening 20 even in the case of the lowest fill levels in the hollow accumulation vessel 7. Secondly, this emergence of process liquid from the hollow accumulation vessel 7 ensures that, should process liquid enter the hollow accumulation vessel 7, the liquid contained therein is always in a flowing movement. The continuous flowing movement advantageously brings about forced mixing of the liquid in the hollow accumulation vessel 7. In turn, this causes the sensor 6 to always measure a mixture of the process liquid present in the hollow accumulation vessel 7 when it carries out a measurement, i.e. not only, for instance, measure a constituent part of a poorly mixed mixture of process liquids in the hollow accumulation vessel 7. Advantageously, this thus avoids separate layering of different liquids in the hollow accumulation vessel 7. Such layering would be inexpedient because this could falsify the measurement of the sensor 6 to the effect of a property of only a constituent part of the liquid present in the hollow accumulation vessel 7 measuring. An exemplary configuration for a lower opening is shown in greater detail in FIG. 5. The embodiment of the lower opening 20 as a slit or slot is only one design option in this case. The explanations provided in this paragraph also apply to differently shaped lower openings 20 provided at least one lower opening 20 extends to the lowermost point of the interior of the hollow accumulation vessel 7.

Figures 3, 3A:
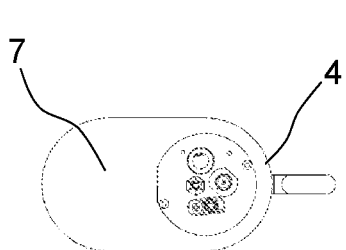
FIG. 3 shows three different embodiments of the measuring apparatus according to the invention with differently designed shapes of the tank and hollow accumulation vessel, wherein each of the three embodiments is shown in turn in three different partial views in each case.
Figures 3, 3B:
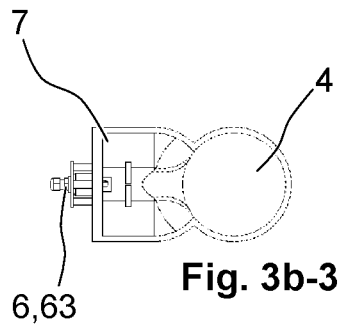
Figures 3, 3C:
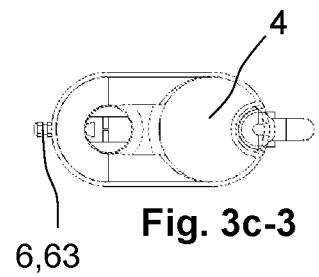

Here, FIGS. 3a-1, 3a-2 and 3a-3 show the same embodiment in different views. FIG. 3a-1 shows an exemplary measuring apparatus 100 in a sectional view from one side, with the inner structure of the measuring apparatus 100 becoming evident. FIG. 3a-2 shows the same exemplary measuring apparatus 100 in a side view. FIG. 3a-3 shows the same exemplary measuring apparatus in a plan view. Analogously, FIGS. 3b, 3c, 4a, 4b and 4c each show a different exemplary embodiment of a measuring apparatus 100, as disclosed here, with these three different views: sectional drawing: −1, side view: −2, plan view: −3.

FIG. 3c shows an exemplary embodiment for a measuring apparatus 100 and a measurement system 300, in which the hollow accumulation vessel 7 is designed as part of the wall of the tank 4, but manufactured as a separate part. By manufacturing the hollow accumulation vessel 7 as a separate part, the production of the measurement system 300 is advantageously simplified and more cost-effective. Thus, for example, the hollow accumulation vessel 7 can initially be equipped with the sensor 6 and subsequently be assembled in liquid-tight fashion in conjunction with the tank 4.

Figures 1, 4A:
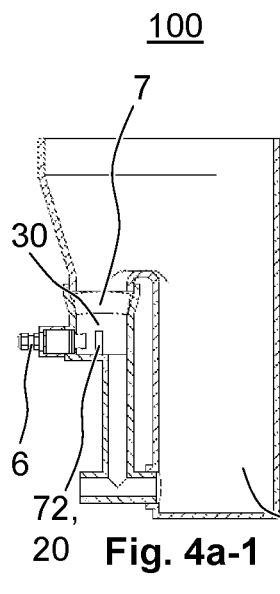
Figures 1, 4B:
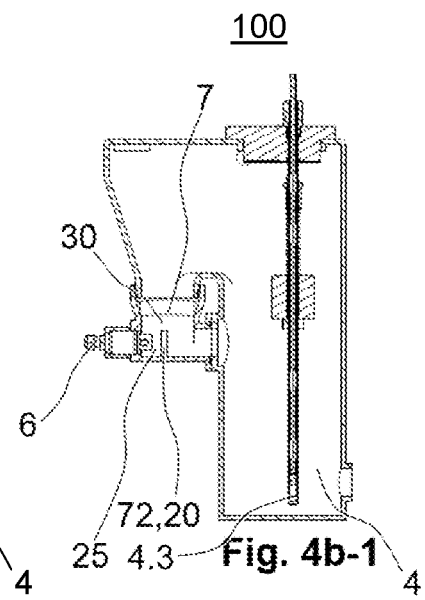

Instead of two fill level limit switches 4.1, 4.2, FIGS. 3a and 4b show an arrangement with an elongate, perpendicularly arranged circuit board with reed sensors for capturing a multiplicity of discrete fill levels.

FIG. 4a shows an exemplary embodiment of a measuring apparatus 100 in which the hollow accumulation vessel 7 was lengthened downward such that it extends parallel to the tank 4 in sections below the lower region 25 and the lower opening 20. Consequently, the outlet connector of the tank 4 is connected to a section of the hollow accumulation vessel 7 and the tank outflow is implemented via the hollow accumulation vessel 7. By way of example, if this embodiment is arranged in the context of a liquid-carrying production system 1000 and a suction pump 10 is connected to the lower connector of the hollow accumulation vessel not connected to the tank 4, there particularly advantageously is greater mixing of process liquids in the hollow accumulation vessel 7 during the operation of the pump because the suction pump 10 partly sucks through the hollow accumulation vessel 7.

FIGS. 4a and 4b show an exemplary embodiment with the same advantages during the manufacture as in the case of the exemplary embodiment shown in FIG. 3c and described above.

Figures 1, 4C:
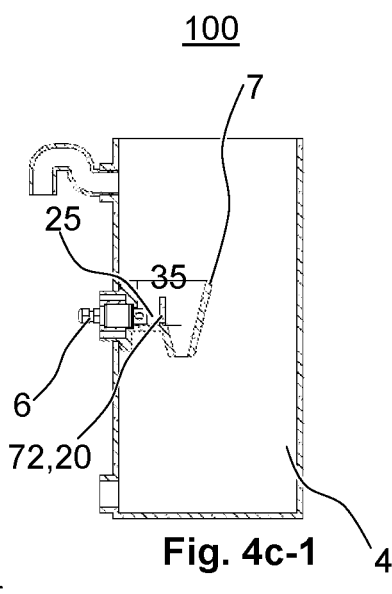
Figures 2, 4A:
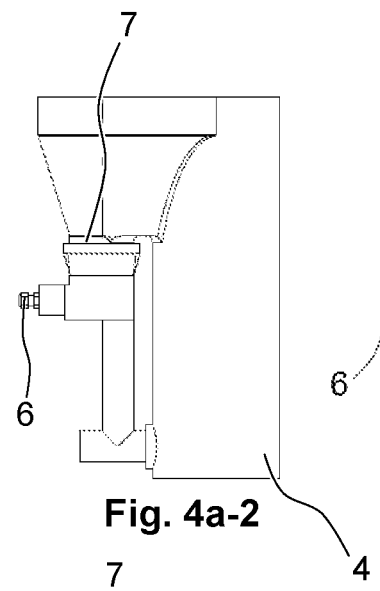
Figures 2, 4B:
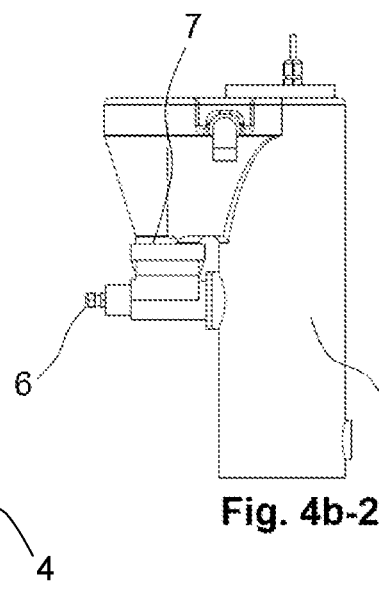
Figures 2, 4C:
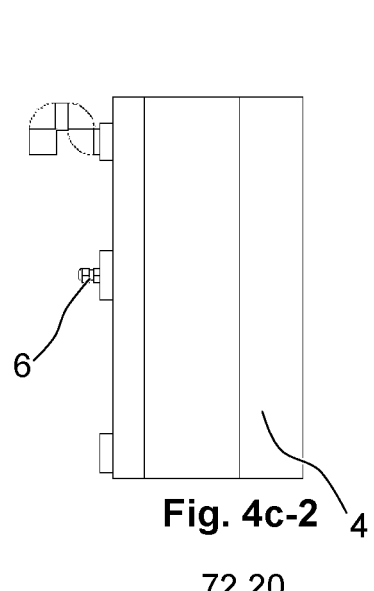
Figures 3, 4A:
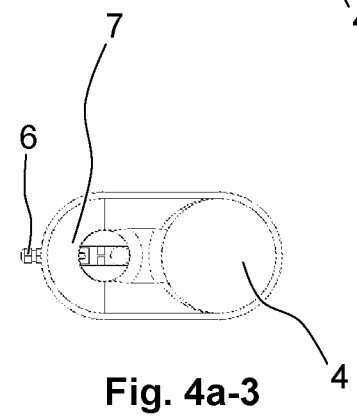
Figures 3, 4B:
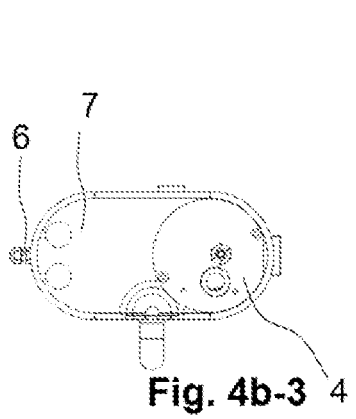
Figures 3, 4C:
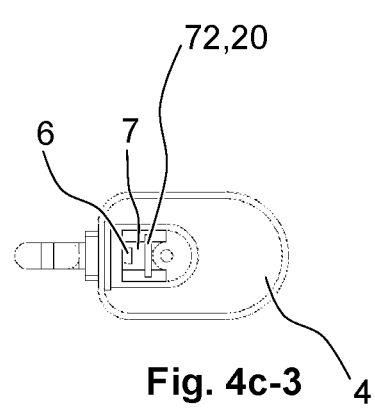

FIG. 4c shows an exemplary embodiment in which the tank 4 has a substantially cylindrical design and the hollow accumulation vessel is arranged on a side wall of the tank 4 so that it is situated completely in the interior of the tank 4. It has a funnel-shaped section.

Figure 5:
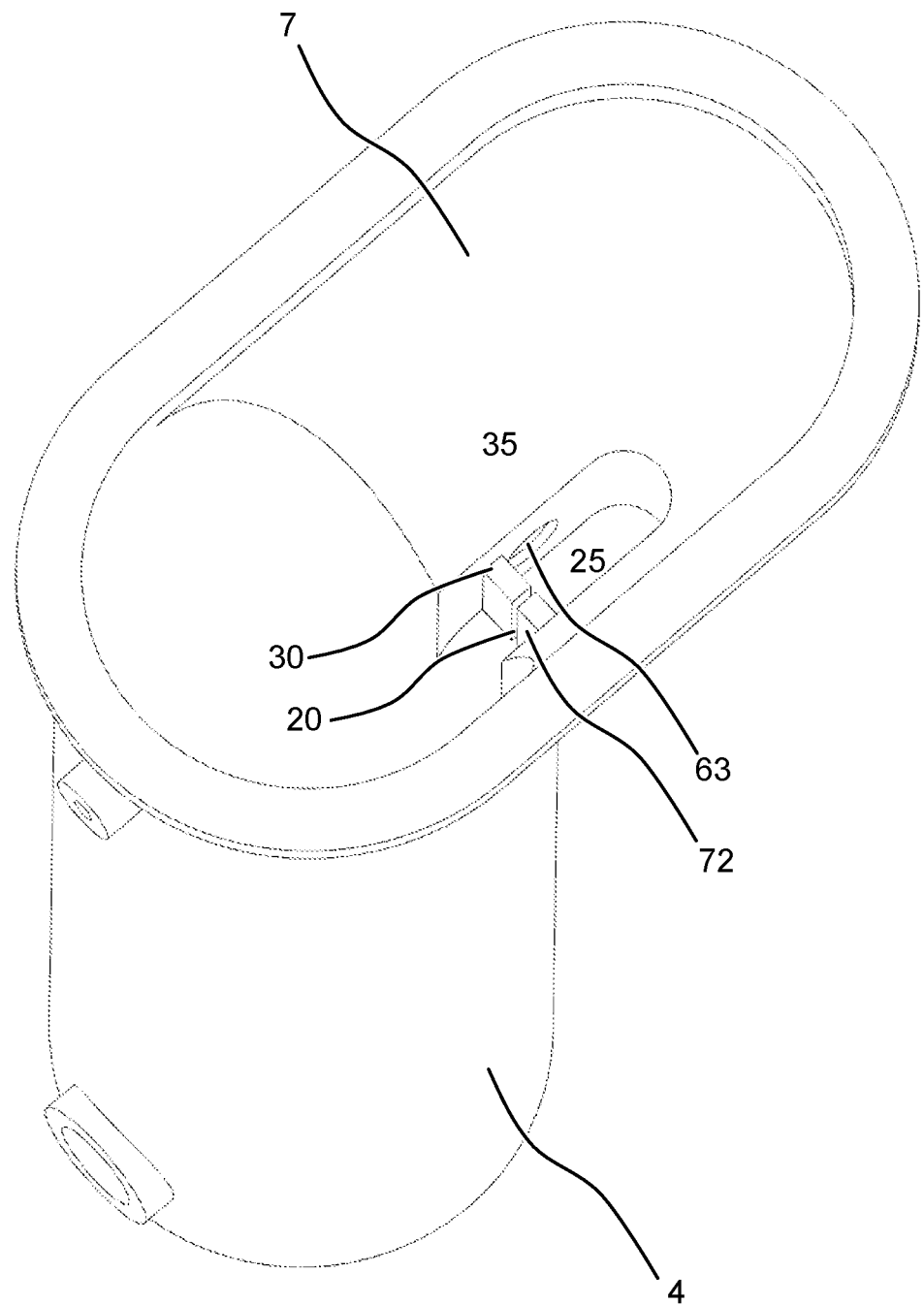
FIG. 5 shows a detailed view looking into the interior of a hollow accumulation vessel and of a tank of an embodiment of a measuring apparatus according to the invention, as also shown in FIGS. 3a-1, 3a-2 and 3a-3 b, with an exemplary design for a lower opening in the lower region and an upper opening in the upper region of the hollow accumulation vessel.

FIG. 5 shows, in a perspective view, viewed from above, the interior of an exemplary measuring apparatus 100 that is identical to the measuring apparatus 100 already shown from three different views in FIGS. 3a-1, 3a-2 and 3a-3. As an example for many embodiments of the measuring apparatus 100, FIG. 5 shows possible designs of the hollow accumulation vessel 7, the tank 4, the lower opening 20 and the upper opening 30. In the embodiment shown, the hollow accumulation vessel 7 is shaped into a side wall of the tank 4. The hollow accumulation vessel 7 has a substantially funnel-shaped cross section and tapers from top to bottom. An opening 63 for receiving the sensor 6 of the measuring apparatus 100 is formed in the side wall in the lower region 25 of the hollow accumulation vessel 7. (The sensor 6 has not been shown for a better illustration herein. Likewise, possible covers and feeding conduits 1 are not shown for a better overview). A lower opening 20 is formed as a slit or slot with a perpendicular extent in the lower region 25 of the hollow accumulation vessel 7. The lower opening 20 merges seamlessly into the upper opening 30. The cross section of the upper opening 30 is more than ten times as large as the cross section of the lower opening 20. In this exemplary embodiment, the upper opening 30 substantially corresponds to the interface between the hollow accumulation vessel 7 with a substantially funnel-shaped design and the cylindrically shaped tank 4, as a result of which the upper opening 30 widens from bottom to top following the cylinder. It is clearly evident that the lower opening 20 is arranged in a wall section 72 in the lower region 25 of the hollow accumulation vessel 7 in this exemplary embodiment. In this exemplary embodiment, the wall section 72 facilitates damming of a liquid in the lower region 25 of the hollow accumulation vessel 7 even in the case of relatively low flow rates. The wall section 72 could also be referred to as a dam wall. In this embodiment, the lower region 25 has a substantially trough-shaped form, with two parallel, perpendicular side walls forming the trough in the longitudinal direction and consequently delimiting the lower region of the measuring apparatus. On the short sides, the lower region 25 is delimited, firstly, by the wall section 72 in which the lower opening 20, formed here as a slit, is situated. The other short side is delimited by a shape corresponding to half a cylinder lateral wall. The upper region 35 starts immediately above the upper edge of the wall section 72 or of the lower opening 25. Here, the upper opening 30 can be imagined as lying in the plane of the wall section 72 but above the wall section 72. If a process liquid fills the lower region 25 and if more liquid than can leave through the lower opening 20 continues to flow into the hollow accumulation vessel 7, the fill level will continue to rise and exceed the upper edge of the lower opening 20 and the wall section 72. Then, the process liquid will flow into the tank 4 of the measuring apparatus 100 through the upper opening 30. This embodiment represents an exemplary option for the geometric design. However, other designs of the hollow accumulation vessel 7 are also possible; these do not require a wall section 72 as the one shown but, for example, operate according to the same principle using, e.g. only openings— for example drilled openings—as one or more lower openings 20 and as one or more upper openings 30. What is essential here is that the sum of the cross sections of all upper openings 30, which are arranged in the upper region 35 of the hollow accumulation vessel 7, have a much greater cross section—for example ten times or one hundred times the cross section—than the lower openings 20 which are arranged in the lower region 25 of the hollow accumulation vessel 7. Since the lower region 25 is located below the upper region 35 and the sensor 6 is arranged in the lower region in all embodiments of the measuring apparatus 100, this allows a property of a process liquid to be measured by the sensor over a large range of flow rates with which the process liquid flows.

Figure 6:
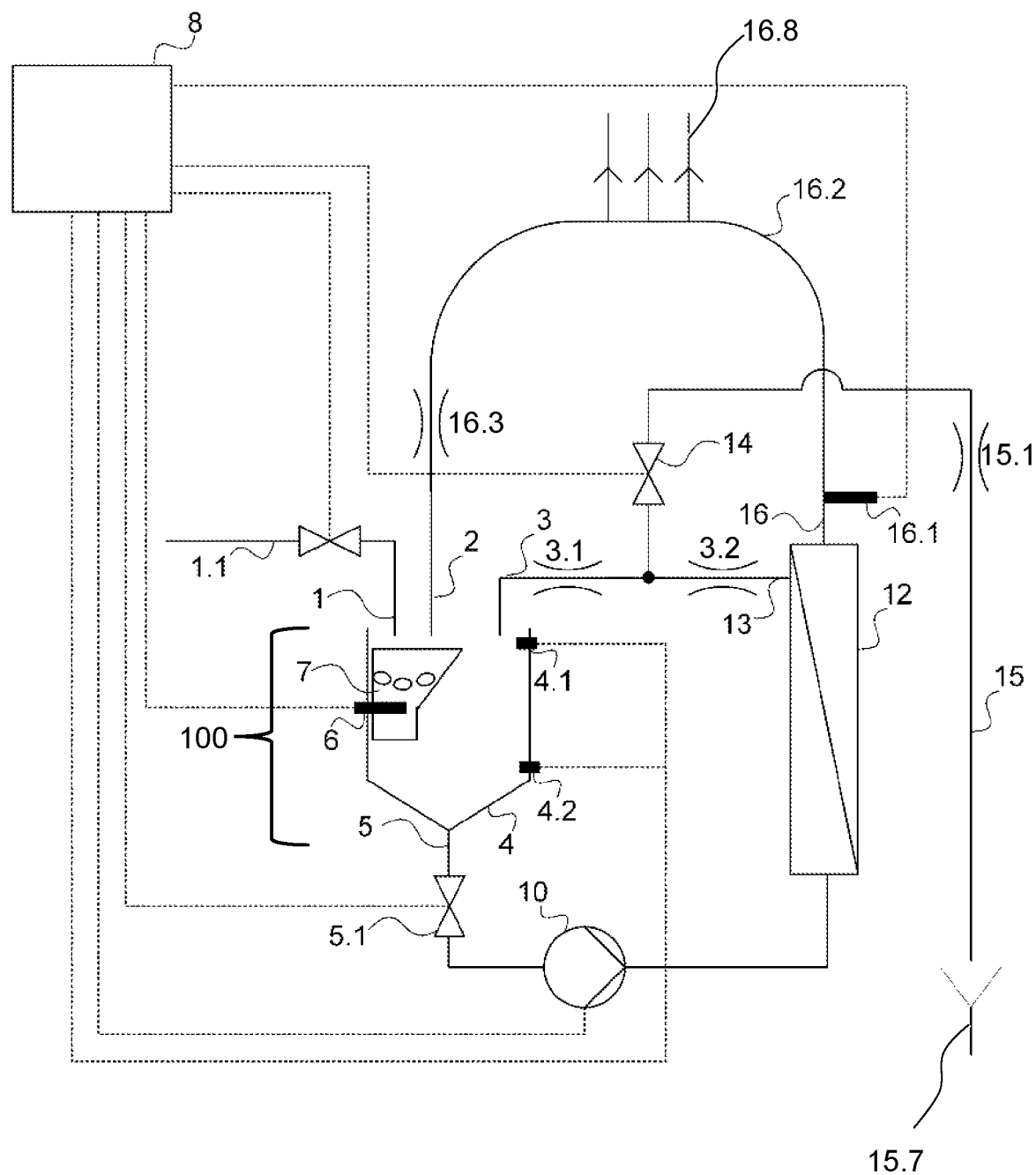
FIG. 6 shows the liquid-carrying production system according to the invention with a measuring apparatus for the online measurement of at least one property of process liquids at at least two different flow rates, having a hollow accumulation vessel in a tank in a first embodiment in a measurement system according to the invention of an exemplary embodiment.

FIG. 6 shows an exemplary embodiment of a liquid-carrying production system 1000 having a measurement system 300 with a measuring apparatus 100. In this example, the liquid-carrying production system 1000 is set up to produce purified water for dialysis by means of reverse osmosis, wherein a pump 10 presses water through a reverse osmosis membrane 12 and consequently certain constituent parts are filtered out of the water. In relation to known production systems, the number of sensors 6, 16.1 was reduced to two by using the measuring apparatus according to the invention: A measuring apparatus 100 with a hollow accumulation vessel 7 and a sensor 6 is set up in the tank 4 for measuring all process liquids upstream of the reverse osmosis membrane 12 and a second sensor 16.1 is set up to measure the produced purified water on the distribution path downstream of the reverse osmosis membrane 12. Here, the measuring apparatus 100 is arranged in the tank 4 in such a way that it is at a level below an upper fill level limit switch 4.1 and below a lower fill level limit switch 4.2. This arrangement makes it possible to detect whether the fill level of the tank 4 is below the measuring apparatus 100 such that the latter only has liquid flowing out of a first or a second conduit 1, 2 (or out of both conduits) flowing therethrough or above the measuring apparatus 100 such that the latter is filled by the mixture of liquids in the tank 4. In this example, soft water is supplied through a first conduit 1 and purified water in the return from the reverse osmosis membrane 12 is supplied through a second conduit 2, in each case into the tank 4 of the measuring apparatus 100 with the hollow accumulation vessel 7. The hollow accumulation vessel 7 has at least one lower opening 20 and at least one upper opening 30, wherein the sum of the cross sections of the upper openings 30 is at least ten times as large as the sum of the lower openings 20 and is adapted to the range of flow rates possible for the various process liquids during operation. A sensor 6 for measuring at least one property of a process liquid is arranged in the measuring apparatus 100. The measuring apparatus 100 is part of a measurement system 300 which comprises a controller 8. The controller 8 is configured to receive a measurement signal from the sensor 6 and control the inflow of various process liquids into the hollow accumulation vessel 7 and/or the tank 4 of the measuring apparatus 100 by virtue of controlling the valve on the first conduit 1 and the valve 14 on the drainage conduit 15 branching from the third conduit 3 and the optional valve 5.1 on the conduit at the drain 5 of the tank 4. Optionally, the controller 8 also controls a pump 10 that is arranged on the conduit at the drain 5 of the tank 4. The distribution path downstream of the purified water side of the reverse osmosis membrane 12 comprises a ring conduit 16.2, to which consumers 16.8, e.g. dialysis machines, can be connected. The unconsumed purified water or dialysis water (or else permeate) arrives back in the tank 4 at the end of the distribution system via a reducer 16.3 and the second conduit 2, in such a way that, when flowing in, it can flow into the hollow accumulation vessel 7 of the measuring apparatus 100. A third conduit 3 guides the so-called concentrate or else retentate, i.e. the water retained at the reverse osmosis membrane 12, back into the tank 4 via a first reducer 3.2 and a second reducer 3.1. Thus, this exemplary embodiment has a connector 13 at the reverse osmosis membrane 12, via which process liquid which reached the reverse osmosis membrane 12 but did not pass through the reverse osmosis membrane 12 is pumped. This process liquid is referred to as retentate since it was retained by the membrane despite flowing over the reverse osmosis membrane. This connector is therefore also referred to as retentate connector. From this connector 13, the third conduit 3 with a first reducer 3.2 and a second reducer 3.1 leads back to the tank and branching therefrom there is a drainage conduit 15, which leads to the drain 15.7 to the sewer system via a valve 14 and a third reducer 15.1. The third conduit 3 guides liquid that has not passed through the membrane, i.e. retentate, back into the tank 4. In the exemplary embodiment shown in FIG. 6, the third conduit 3 is a specific conduit for returning the retentate into the tank 4 and is arranged such that the retentate does not directly reach the measuring apparatus 100 but only reaches the latter indirectly via an accumulation procedure in the tank 4, either individually or mixed with the other process liquids present in the tank 4. This arrangement is optional. Alternatively, the third conduit 3 can also be arranged in such a way that the retentate can directly reach the hollow accumulation vessel 7 of the measuring apparatus 100, wherein a freefall path, for example, can be provided between the end of the third conduit 3. In this embodiment, a freefall path is shown for the first conduct 1 and the second conduct 2, between their output at the end and the hollow accumulation vessel 7 of the measuring apparatus 100, and between the third conduct 3 and the tank 4. The controller 8 can be set up with hardware components and software components for electronic data capture and data processing for the measurement data and for controlling the production system 1000.

Figure 7:
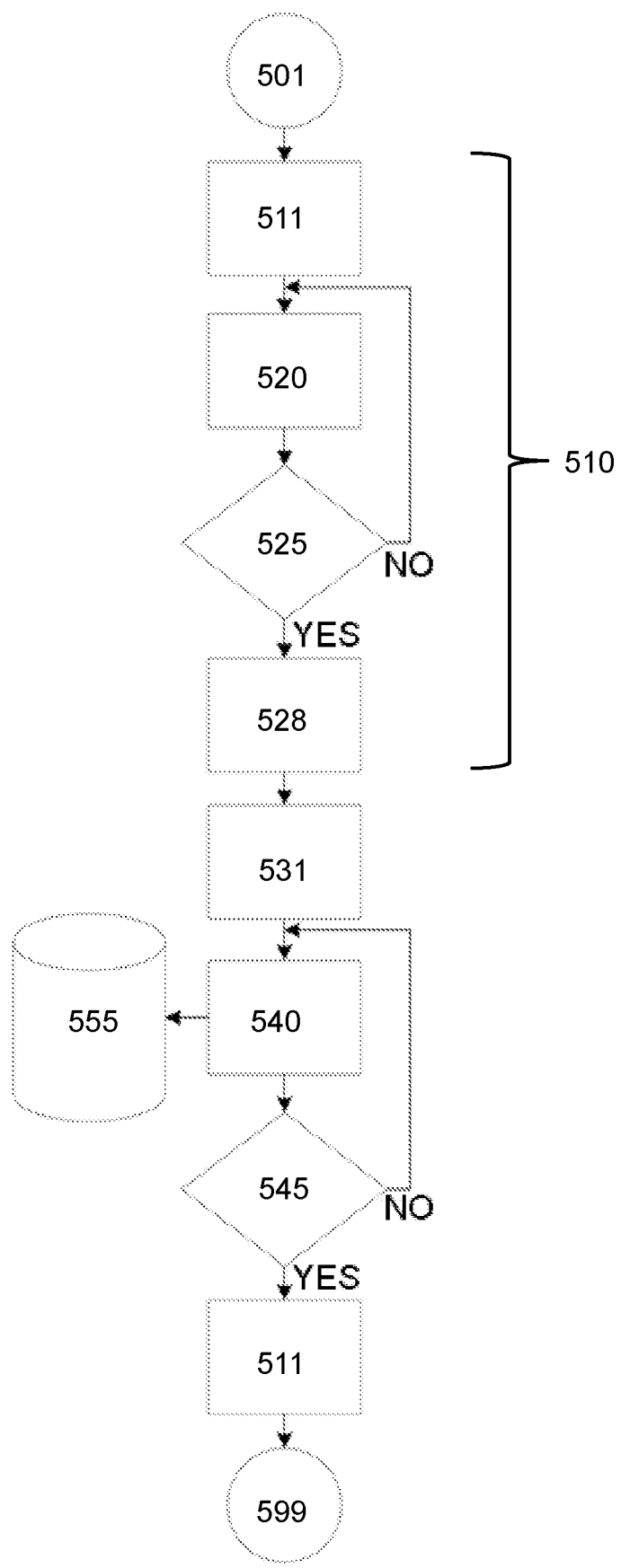
FIG. 7 shows the method according to the invention for separately measuring at least one property of at least two different process liquids using the same sensor in an exemplary embodiment, in which the fill level in the tank is lowered and the process liquid to be measured is fed to the sensor by way of a feed conduit.

FIG. 7 shows an exemplary method procedure for a method 500 according to the invention for separately measuring at least one property of a process liquid. In practice, different process liquids of, e.g. liquid-carrying production systems 1000 will almost always have different flow rates. However, the method is also applicable if, perchance, in an operational situation the two liquids have almost identical flow rates, flow rates that are identical down to decimal places or flow rates that are identical within the scope of measurement accuracy. The method can be carried out using a measuring apparatus 100, a measurement system 300 or a liquid-carrying production system 1000 according to the invention and includes at least the following steps:

a. separately feeding 531, 532 the process liquid to be measured to the sensor 6 in the hollow accumulation vessel 7,
b. measuring 540 a property of the process liquid in contact with the sensor 6 until a predetermined minimum measurement time has been reached 545,
c. storing 555 the measurement value of the property of the process liquid after the predetermined minimum measurement time has been reached.

Below, the method, as can be carried out using a measurement system 300 with fill level limit switches 4.2 and 4.1, as shown in FIGS. 1, 2 and 6, is described in exemplary fashion. However, the method is also possible using a measuring apparatus 100 according to the invention installed in another apparatus.

In this exemplary embodiment, the fill level in the tank 4 is initially lowered 510 in a plurality of steps 511, 520, 525, 528 until the fill level lies below the hollow accumulation vessel in order to allow the liquid to be measured to be fed 531 separately to the sensor 6. A controlled separate feed of a process liquid to be measured is essential to the invention. However, lowering 510 the fill level is only one of a plurality of options. It should also be noted that the so-called feedwater or mixed water is also considered a separate process liquid in the context of the invention, even though this is a mixture of a plurality of process liquids. To this end, the feed 1.1 is blocked in a first step 511 following the start 501 of the method 500. Then, the fill level in the tank 4 is lowered by virtue of removing 520 liquid from the tank 4. How the liquid is removed 520 from the tank 4 is irrelevant to the method 500. By way of example, removing 520 the liquid from the tank 4 in the case of an apparatus 100 such as the measurement system 100 of FIG. 1 would mean that liquid flows out of the tank 4 at the bottom through the so-called tank outflow 5 and the outflow valve 5.1 is open. By way of example, the removal 520 in the case of a liquid-carrying production system 1000 as shown in FIG. 6 can be implemented by a drainage conduit 15 from the outflow valve 5.1 to a drain 15.7—e.g. to the sewer system. Removing the liquid from the tank 520 is continued until the fill level of the lower fill level limit switch 4.2 is reached 528. As soon as this is the case, the pump 10 is deactivated 528 and the feed 1.1 is opened in the next step 531. Now, measuring 540 a property of the liquid using the sensor 6 is commenced. By way of example, temperature and conductivity are measured here. The measurement 540 is continued until the minimum capture time has been reached 545. Then, the measurement data are stored 555. As soon as this is the case, the feed 1.1 is blocked 511 and the measuring method 500 is complete 599.

Figure 8:
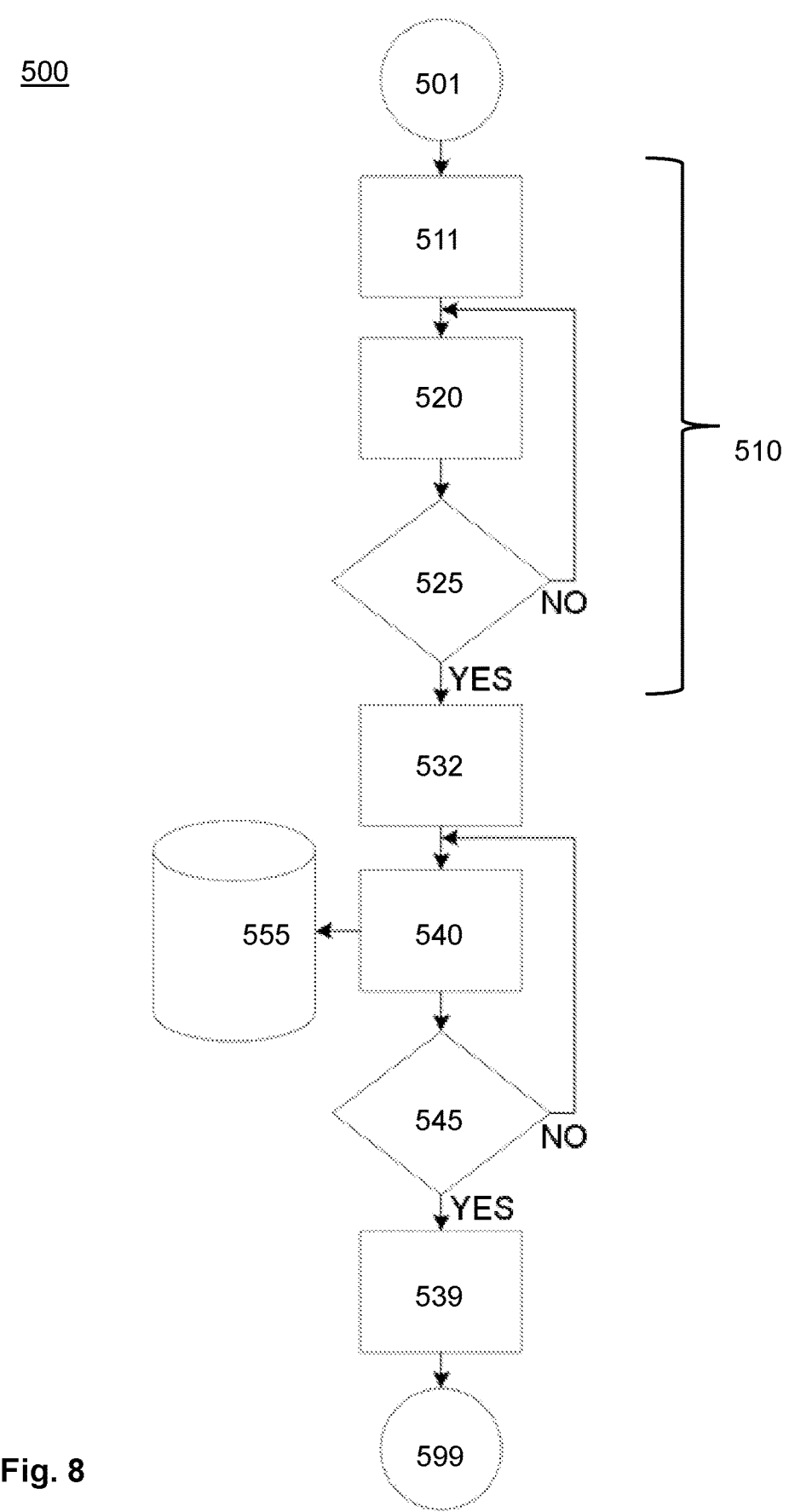
FIG. 8 shows the method according to the invention for separately measuring at least one property of at least two different process liquids using the same sensor in an exemplary embodiment, in which the fill level in the tank is lowered and the process liquid to be measured is fed to the sensor by way of a circulation.

FIG. 8 shows an exemplary method procedure for a method 500 according to the invention for separately measuring at least one property of a process liquid. Like in the exemplary embodiment shown in FIG. 7, the fill level in the tank 4 is initially lowered 510 in a plurality of steps 511, 520, 525, 528 until the fill level lies below the hollow accumulation vessel in order to allow the liquid to be measured to be fed 531 separately to the sensor 6. In contrast to the exemplary embodiment of FIG. 7, the process liquid to be measured is fed 532 here to the sensor 6 by circulating the process liquid. For illustrative purposes, the method steps are explained in such a way here that they are carried out in exemplary fashion using a measurement system 300 with a measuring apparatus 100 like in a liquid-carrying production system 1000 shown in FIG. 6; however, the method 500 is not restricted to the implementation with these apparatuses 100, 300, 1000 but can also be carried out using other apparatuses. Since the exemplary liquid-carrying production system 1000 shown in FIG. 6 exhibits an embodiment of how a reverse osmosis installation—having the measuring apparatus 100 disclosed here and the measurement system 300 disclosed here—operates, some terms in the explanation relating to FIG. 8 are specific to reverse osmosis installations. When carrying out the method 500 disclosed here with a different liquid-carrying production system 1000, for example a mixing installation for producing dialysis concentrate, the terms for the apparatus constituent parts must in part be adapted accordingly.

Initially, the fill level in the tank 4 is lowered 510 in a plurality of steps 511, 520, 525, 528 until the fill level is below the hollow accumulation vessel. To this end, the valve 1.1 in the first conduit 1 is blocked in a first step 511 following the start 501 of the method 500, and so no process liquid flows into the tank 4 through this conduit 1. Then, liquid is removed from the tank 4 in a second step 520 until a check in a third step 525 yields that the fill level in the tank 4 is lower than the measuring apparatus 100. This ensures for the subsequent course of the method 500 that it is not dammed liquid possibly present in the tank 4 that is measured. An example for a high fill level is shown in FIG. 2c for a measurement system 300 with a measuring apparatus 100. In the exemplary embodiment of FIG. 6, the valve 5.1 at the drain 5 of the tank 4 is opened and the pump 10 arranged downstream thereof is switched on for the purposes of lowering 510 the fill level in the removal step as per method step 520, as a result of which process liquid possibly present in the tank 4 reaches the upstream side of the reverse osmosis membrane 12. However, the exact design of the apparatus is irrelevant to the method. Therefore, there also is no more in-depth discussion here in respect of which further actions are carried out in the case of the exemplary apparatus 1000 of FIG. 6 so that the liquid reaches a drain 15.7 via the drainage conduit 15, or how reducers 3.2, 3.1 have to be designed so that the liquid reaches the drain 15.7. In this exemplary embodiment and in the exemplary embodiment of FIG. 6, there is a connector 13 at the reverse osmosis membrane 12, via which process liquid which reached the reverse osmosis membrane 12 but did not pass through the reverse osmosis membrane 12 is pumped. This process liquid is referred to as retentate since it was retained by the membrane 12 despite flowing over the reverse osmosis membrane 12. This connector 13 is therefore also referred to as retentate connector 13. From this connector 13, a third conduit 3 with a first reducer 3.2 and a second reducer 3.1 leads back to the tank 4 and branching therefrom there is a drainage conduit 15, which leads to the drain 15.7 to the sewer system via a valve 14 and a third reducer 15.1. The third conduit 3 guides liquid that has not passed through the membrane, i.e. retentate, back into the tank 4.

The valve 14 in the course of the branching conduit 15 to the drain 15.7 into the sewage system is opened and so liquid transported by the pump 10, which has not passed through the reverse osmosis membrane 12, reaches the sewer system via the branching conduit 15 to the drain 15.7. Moreover, an optional further reducer 15.1 of the branching conduit 15 to the drain 15.7 into the sewer system is shown along the conduit. As a result of this configuration and the operation of the pump 10, the fill level of the tank 4 falls, provided it was previously above the lower fill level limit switch 4.2, and the lower fill level limit switch 4.2 will recognize when the fill level has fallen to below the fill level limit switch 4.2. FIG. 2b shows this state for one exemplary embodiment. The pump 10 is operated until the lower fill level limit switch 4.2 recognizes a fill level situated therebelow. As soon as this is the case, the valve 14 at the conduit 15 to the drain 15.7 to the sewer system, which conduit branches from the third conduit 3, is closed and the pump 10 continues operation. As a consequence, the pump 10 circulates process liquid in the second conduit 2, which has passed through the reverse osmosis membrane and which leads to the distribution conduit 16, 16.2 on the downstream side of the membrane 12, which then finally becomes the second conduit 2 during the return to the tank 4. As a result of this circulation, the process liquid to be measured, i.e. purified water that has passed through the membrane 12 in this case, is fed separately to the sensor 6. At the same time, the pump 10 circulates process liquid in the third conduit 3, which discharges process liquid that has not passed through the reverse osmosis membrane at the upstream side 13 of the reverse osmosis membrane.

Figure 9:
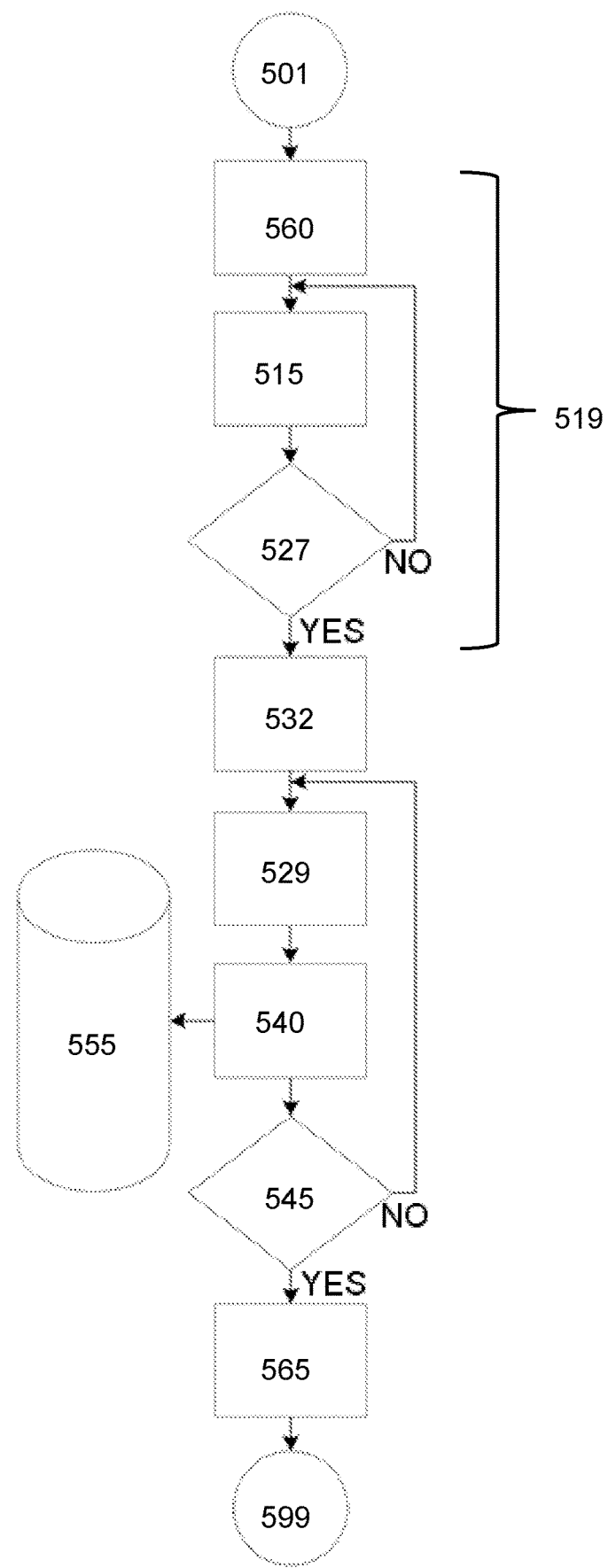
FIG. 9 shows the method according to the invention for separately measuring at least one property of at least two different process liquids using the same sensor in an exemplary embodiment, in which the fill level in the tank is raised and hence the process liquid to be measured is fed to the sensor.

FIG. 9 shows an exemplary method procedure for a method 500 according to the invention for separately measuring at least one property of a process liquid. In contrast to the methods 500 shown in FIGS. 7 and 8, the fill level in the tank 4 is raised 519 in a plurality of steps 560, 515, 527 in this exemplary embodiment until the fill level is at least above the sensor 6 or above the hollow accumulation vessel, and hence the liquid to be measured is fed 532 separately to the sensor 6.

The method can be carried out using a measuring apparatus 100, a measurement system 300 or a liquid-carrying production system 1000 according to the invention and includes at least the following steps:
- activating the production operation of reverse osmosis 560, i.e. implementing an operation that conveys water through the reverse osmosis membrane 12,
- opening 15 the feed conduit for soft water 1.1,
- continuing this procedure until an upper fill level has been reached 527, i.e. for example until an upper fill level limit switch 4.1 triggers.

Hence, the liquid accumulated in the tank 4 has been fed to the sensor 6. Optionally, this is followed by a further step 529, in which the apparatus is controlled such that the fill level in the tank 4 remains substantially unchanged, i.e. continues to trigger the upper fill level limit switch 4.1. This can be continued until a measurement 540 has reached 545 a predetermined minimum time for the measurement. Then, the measurement value is stored 555 and the production operation of reverse osmosis, i.e. the conveying operation, can be terminated 565.

Figure 10:
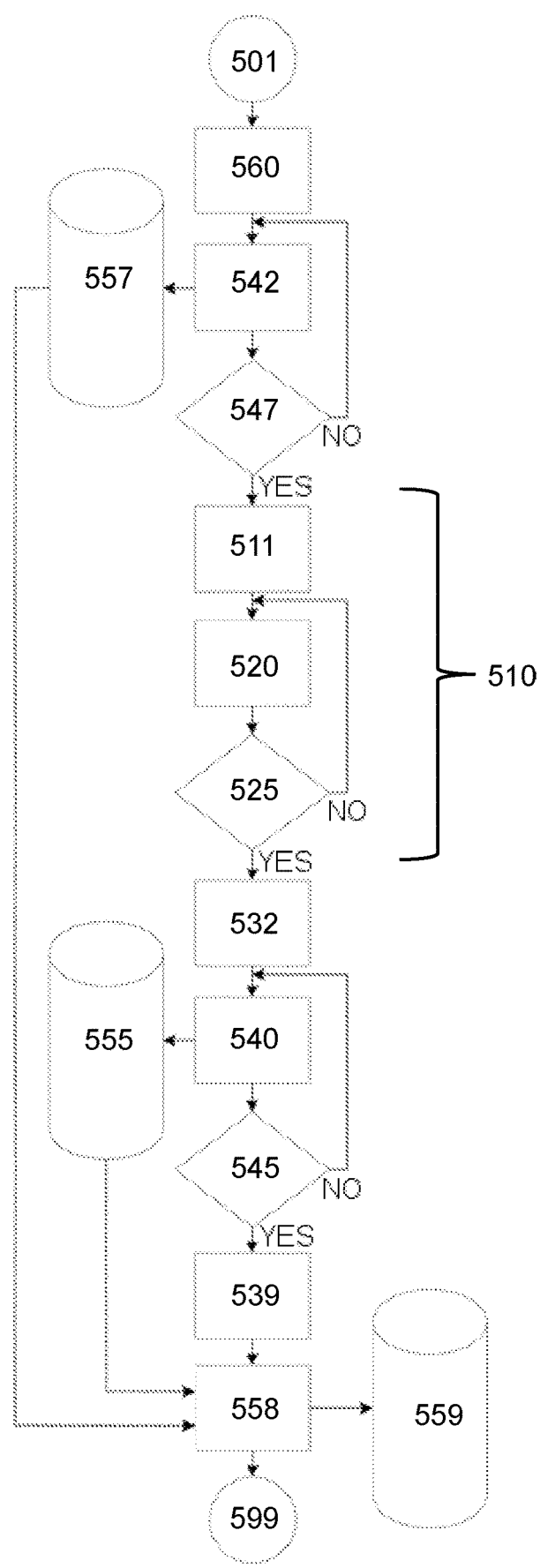
FIG. 10 shows a method according to the invention for separately measuring at least one property of at least two different process liquids using the same sensor in an exemplary embodiment, in which a measurement of the same property of the same liquid is additionally implemented using a second sensor.

FIG. 10 shows an exemplary method procedure for a method 500 according to the invention for separately measuring at least one property of a process liquid and for comparison with a second sensor 16.1.

Here, in addition to the steps of separately feeding 531, 532 the process liquid to be measured to the sensor 6 in the hollow accumulation vessel 7, measuring 540 a property of the process liquid in contact with the sensor 6 until a predetermined minimum measurement time has been reached 545 and storing 555 the measurement value of the property of the process liquid after reaching the predetermined minimum measurement time, this embodiment of the method according to the invention comprises at least the following steps:
a. separately feeding the process liquid to be measured to the second sensor 16.1,
b. measuring 542 the same property of the process liquid in contact with the second sensor 16.1 until a predetermined minimum measurement time has been reached 547,
c. storing 557 the measurement value of the property of the process liquid after the predetermined minimum measurement time has been reached,
d. comparing 558 the measurement values of the two sensors 6, 16.1.

Optionally, this can be followed by an assessment of the result of the comparison 558.

Optionally, the result of the comparison 558 is stored 559.

It is possible to combine this embodiment of the method 500 with a method 500 as shown in FIGS. 7, 8 and 9.

In one embodiment of the method, described in exemplary fashion with reference to the liquid-carrying production system of FIG. 6, a process liquid can be fed 560 to the second sensor 16.1 by virtue of the production operation of a reverse osmosis installation being activated and hence a process liquid being fed to a reverse osmosis membrane 12. The liquid that has passed through the reverse osmosis membrane 12 is fed to a second sensor 16.1 downstream of the reverse osmosis membrane 12. Then, a property of the process liquid in contact with the second sensor 16.1 is measured 542 until a predetermined minimum measurement time 547 has been reached. The measurement value is stored 557 after the predetermined minimum measurement time 547 has been reached. Then, this is followed by lowering 510 of the fill level in the tank 4 in a plurality of partial steps until said fill level is below the hollow accumulation vessel 7. This is adjoined by steps like in the method shown in FIG. 8: The process liquid remaining in the tank is fed to a reverse osmosis membrane 12 and the liquid that has passed through the reverse osmosis membrane 12 is fed 532 to the sensor 6, this is followed by measuring 540 a property of the process liquid in contact with the sensor 6 until a predetermined minimum measurement time has been reached 545, storing 555 the measurement value of the second sensor 6 after the predetermined minimum measurement time has been reached, and comparing 558 the measurement values of the two sensors 6, 16.1.

Optionally: storing 559 the comparison of the two measurement values.

The invention claimed is:

1. A measuring apparatus for the online measurement of at least one property of process liquids at least two different flow rates and during the production of a medical liquid, comprising:
a. a tank for receiving the process liquid, wherein the tank has an outflow,
b. a hollow accumulation vessel which
  i. is arranged within the tank, in a side wall of the tank or on a side wall of the tank,
  ii. depending on the fill level in the tank can have process liquid pass therethrough, can be entirely filled by process liquid or can be partly filled by process liquid,
  iii. comprises at least one lower opening, which is arranged in the lower region of the hollow accumulation vessel and fluidically connected to the interior of the tank, and through which opening process liquid stored in the hollow accumulation vessel is able to flow into the tank in the case where a fill level of the tank is lower than the fill level in the hollow accumulation vessel,
  iv. comprises at least one upper opening, which is arranged in the upper region of the accumulation vessel and fluidically connected to the interior of the tank such that additionally process liquid can overflow out of the hollow accumulation vessel through the at least one upper opening into the tank when the fill level of the process liquid in the hollow accumulation vessel reaches up to the at least one upper opening,
   v. wherein the upper region is located above the lower region,
   vi. wherein the sum of the cross sections of the at least one upper openings is at least ten times as large as the sum of the cross sections of the at least one lower openings,
  c. a sensor for measuring at least one property of the process liquid, which sensor is arranged in the hollow accumulation vessel in such a way that it can be in contact with the process liquid when process liquid accumulates in the hollow accumulation vessel,
  d. at least two conduits are equipped with control valves for feeding at least two different process liquids into the tank,
  e. at least two means are provided for controlling the feed or discharge of process liquids into the tank through control valves,
  f. a controller configured to capture the measurement values of the sensor and control the valves.

2. The measuring apparatus according to claim 1, wherein the sensor is a conductivity sensor or temperature sensor.

3. The measuring apparatus according to claim 1, wherein two or more sensors are arranged together in the hollow accumulation vessel for the purposes of measuring different properties of the process liquid.

4. The measuring apparatus according to claim 3, wherein a conductivity sensor and a temperature sensor are arranged together in the hollow accumulation vessel.

5. The measuring apparatus according to claim 1, wherein the hollow accumulation vessel has a shape that tapers from top to bottom, a funnel shape or a cylindrical shape.

6. The measuring apparatus according to claim 1, wherein the at least two conduits are arranged so that a freefall path is formed between their outlet openings at the end and the hollow accumulation vessel.

7. The measuring apparatus according to claim 3, comprising one or more of the following means for identifying which process liquid is in contact with the sensor of the measuring apparatus:
  a. at least one means for determining the fill level in the tank, which means is able to identify more than two differently high fill levels in the tank,
  b. or at least two fill level limit switches which are set up to determine a lower and an upper fill level in the tank,
  c. or the controller is set up to control the flow of the different process liquids in a certain time sequence so that the current process liquid can be determined on the basis of the time profile,
  d. or, if the measurement region of the properties of the process liquid is non overlapping for the different properties of process liquids, the controller is set up to carry out an assignment of measurement value to process liquids on the basis of the measurement value of the sensor and known measurement regions for different process liquid.

8. A liquid carrying production system for producing medical liquids, comprising the measuring apparatus according to claim 1.

9. The liquid carrying production system according to claim 8, which is embodied as a water treatment installation or a purified water preparation installation for providing dialysis water, wherein the measuring apparatus is arranged in a reservoir tank of the production system.

10. The liquid carrying production system according to claim 8, which is embodied as a mixing installation for providing dialysis fluid or dialysis fluid concentrate, wherein the measuring apparatus is arranged in a reservoir tank or mixing tank of the production system.

11. The liquid carrying production system according to claim 9, which is embodied as a reverse osmosis installation.

12. A method of separately measuring at least one property of a process liquid using the measuring apparatus according to claim 1 or the liquid carrying production system according to claim 8, comprising at least the following steps:
  a. separately feeding the process liquid to be measured to the sensor in the hollow accumulation vessel,
  b. measuring a property of the process liquid in contact with the sensor until a predetermined minimum measurement time has been reached,
  c. storing the measurement value of the property of the process liquid after the predetermined minimum measurement time has been reached.

13. The method according to claim 12, wherein the separate feed is implemented with at least the following steps:
  a. lowering the fill level in the tank until the fill level is below the hollow accumulation vessel,
  b. releasing the conduit for feeding the process liquid to be measured into the hollow accumulation vessel.

14. The method according to claim 12, wherein the separate feed is implemented with at least the following step:
  raising the fill level in the tank up to a fill level that is level with the sensor or higher.

15. A method of separately measuring at least one property of at least two different process liquids with the same sensor, wherein successively in an interchangeable sequence at least one property of a first process liquid is measured using the method according to claim 14 and at least the same property of a second process liquid is measured using a method according to claim 14 or wherein a second process liquid is fed again following the second step of the method according to claim 13, releasing the conduit for the feed.

16. The method according to claim 13, wherein lowering the fill level in the tank is followed by the separate feed by virtue of the process liquid remaining in the tank being guided to a reverse osmosis membrane and either the liquid that passed through the reverse osmosis membrane or the process liquid that did not pass through the reverse osmosis membrane being fed to the sensor.

17. A method of separately measuring at least one property of a process liquid according to claim 12 and for a comparison with a second sensor, additionally comprising at least the following steps:
  a. separately feeding the process liquid to be measured to the second sensor,
  b. measuring the same property of the process liquid in contact with the second sensor until a predetermined minimum measurement time has been reached,
  c. storing the measurement value of the property of the process liquid after the predetermined minimum measurement time has been reached, d. comparing the measurement values of the two sensors.

18. The measurement system or the liquid carrying production system, comprising a controller configured to carry out the method according to claim 12.

* * * * *